(12) United States Patent
McGrath et al.

(10) Patent No.: US 11,647,903 B2
(45) Date of Patent: May 16, 2023

(54) SMARTPHONE-BASED DIGITAL PUPILLOMETER

(71) Applicant: University of Washington, Seattle, WA (US)

(72) Inventors: Lynn B. McGrath, Seattle, WA (US);
Anthony Law, Seattle, WA (US);
Randall Bly, Seattle, WA (US);
Shwetak N. Patel, Seattle, WA (US);
Alex T. Mariakakis, Seattle, WA (US);
Jacob Baudin, Seattle, WA (US)

(73) Assignee: University of Washington, Seattle, WA (US)

( * ) Notice: Subject to any disclaimer, the term of this patent is extended or adjusted under 35 U.S.C. 154(b) by 511 days.

(21) Appl. No.: 16/618,044

(22) PCT Filed: May 31, 2018

(86) PCT No.: PCT/US2018/035432
§ 371 (c)(1),
(2) Date: Nov. 27, 2019

(87) PCT Pub. No.: WO2018/222897
PCT Pub. Date: Dec. 6, 2018

(65) Prior Publication Data
US 2020/0129063 A1    Apr. 30, 2020

Related U.S. Application Data

(60) Provisional application No. 62/513,808, filed on Jun. 1, 2017.

(51) Int. Cl.
*A61B 3/14*    (2006.01)
*G06N 20/00*    (2019.01)
(Continued)

(52) U.S. Cl.
CPC ............ *A61B 3/145* (2013.01); *A61B 3/0008* (2013.01); *A61B 3/11* (2013.01); *A61B 5/4064* (2013.01);
(Continued)

(58) Field of Classification Search
CPC ....... A61B 3/113; A61B 5/0077; A61B 3/112; A61B 5/163; A61B 3/145; A61B 3/0008;
(Continued)

(56) References Cited

U.S. PATENT DOCUMENTS 5,187,506 A    2/1993  Carter
8,235,526 B2   8/2012  Stark et al.
(Continued)

FOREIGN PATENT DOCUMENTS

CA    2924546 A1 *  3/2015  ............. A61B 3/112
CN    102682305 B  *  7/2014
(Continued)

OTHER PUBLICATIONS

Tensity Research Based on the Information of Eye Movement—2014 (Year: 2014).*
(Continued)

*Primary Examiner* — Nizar N Sivji
(74) *Attorney, Agent, or Firm* — Christensen O'Connor Johnson Kindness PLLC

(57) ABSTRACT

In some embodiments, techniques for using machine learning to enable visible light pupilometry are provided. In some embodiments, a smartphone may be used to create a visible light video recording of a pupillary light reflex (PLR). A machine learning model may be used to detect a size of a pupil in the video recording over time, and the size over time may be presented to a clinician. In some embodiments, a system that includes a smartphone and a box that holds the smartphone in a predetermined relationship to a subject's (Continued)

face is provided. In some embodiments, a sequential convolutional neural network architecture is used. In some embodiments, a fully convolutional neural network architecture is used.

14 Claims, 15 Drawing Sheets

(51) Int. Cl.
  *A61B 3/00* (2006.01)
  *A61B 3/11* (2006.01)
  *A61B 5/00* (2006.01)
  *G06N 3/04* (2006.01)
  *G06N 3/08* (2006.01)
  *G06V 40/18* (2022.01)

(52) U.S. Cl.
  CPC .............. *G06N 3/0454* (2013.01); *G06N 3/08* (2013.01); *G06N 20/00* (2019.01); *G06V 40/193* (2022.01)

(58) Field of Classification Search
  CPC ........... A61B 3/11; A61B 5/4064; A61B 3/00; G06N 20/00; G06N 3/02; G06N 3/0454; G06N 3/08; G06V 10/82; G06V 40/20; G06V 40/197; G06V 40/193; G06V 40/19
  See application file for complete search history.

(56) References Cited

U.S. PATENT DOCUMENTS

| | | | | |
|---|---|---|---|---|
| 8,248,458 | B2* | 8/2012 | Schowengerdt | G02B 26/005 348/51 |
| 9,888,845 | B2 | 2/2018 | Visconti | |
| 10,034,605 | B2 | 7/2018 | Holt et al. | |
| 10,070,787 | B2 | 9/2018 | Visconti | |
| 2005/0165327 | A1 | 7/2005 | Thibault et al. | |
| 2009/0163777 | A1 | 6/2009 | Jung et al. | |
| 2009/0306538 | A1 | 12/2009 | Siminou | |
| 2015/0098630 | A1 | 4/2015 | Perna et al. | |
| 2015/0116665 | A1* | 4/2015 | Finkel | A61B 3/112 351/210 |
| 2015/0160726 | A1* | 6/2015 | Sullivan | G06V 40/19 345/156 |
| 2015/0282705 | A1* | 10/2015 | Avital | A61B 3/113 600/301 |
| 2016/0103338 | A1 | 4/2016 | Hart et al. | |
| 2016/0117587 | A1 | 4/2016 | Yan et al. | |
| 2016/0210503 | A1* | 7/2016 | Yin | G06T 7/73 |
| 2016/0262611 | A1 | 9/2016 | Rotenstreich | |
| 2017/0100032 | A1* | 4/2017 | Zakariaie | A61B 3/145 |
| 2017/0105669 | A1 | 4/2017 | Valenti | |
| 2017/0231515 | A1 | 8/2017 | Pedro | |
| 2017/0235931 | A1* | 8/2017 | Publicover | H04L 63/0861 |
| 2017/0293356 | A1* | 10/2017 | Khaderi | G06F 3/147 |

FOREIGN PATENT DOCUMENTS

| | | | |
|---|---|---|---|
| CN | 106778567 A | 5/2017 | |
| CN | 106778567 B * | 5/2019 | |
| WO | 2015/063598 A1 | 5/2015 | |
| WO | 2015063598 A1 | 5/2015 | |
| WO | 2016/179370 A1 | 11/2016 | |
| WO | 2016179370 A1 | 11/2016 | |
| WO | 2017/062777 A1 | 4/2017 | |
| WO | 2017062777 A1 | 4/2017 | |
| WO | WO-2018063451 A1 * | 4/2018 | ........... G06K 9/0061 |
| WO | 2018/134814 A1 | 7/2018 | |
| WO | 2018/142388 A1 | 8/2018 | |

OTHER PUBLICATIONS

Two competitive solutions to the problem of remote Eye-Tracking—2009 (Year: 2009).*
PupilNet: Convolutional Neural Networks for Robust Pupil Detection—2016 (Year: 2016).*
A free geometry model-independent neural eye-gaze tracking system—2012 (Year: 2012).*
Retinal Imaging and Image Analysis—2010 (Year: 2010).*
Accurate Eye Center Location through Invariant Isocentric Patterns—2012 (Year: 2012).*
Eye movement Measure System and its Applications—2010 (Year: 2010).*
In the Eye of the Beholder: A Survey of Models for Eyes and Gaze—2010 (Year: 2010).*
Probabilistic Approach to Robust Wearable Gaze Tracking—2017 (Year: 2017).*
Abdolvahabi, A., et al., "Colorimetric and Longitudinal Analysis of Leukocoria in Recreational Photographs of Children with Retinoblastoma", PLOS ONE, vol. 8, Issue 10, e76677, 1-14, Oct. 2013.
Mariakakis, A., et al., "PupilScreen: Using Smartphones to Assess Traumatic Brain Injury", Proceedings of the ACM on Interactive, Mobile, Wearable and Ubiquitous Technologies, 1(3), Article 81, 1-3, Sep. 2017.
Bastawrous, A., et al., "Development and Validation of a Smartphone-Based Visual Acuity Test (Peek Acuity) for Clinical Practice and Community-Based Fieldwork". JAMA Ophthalmol., 133(8), 930-937, 2015.
Behrends, M., et al., "Infrared pupillometry to detect the light reflex during cardiopulmonary resuscitation: A case series", Resuscitation, 83, 1223-1228, 2012.
Boden, B., et al., "Catastrophic Head Injuries in High School and College Football Players", The American Journal of Sports Medicine, 35(7), 1075-1081, 2007.
Broglio, S., et al., "Test-Retest Reliability of Computerized Concussion Assessment Programs", Journal of Athletic Training, 42(4), 509-514, 2007.
Capó-Aponte, J., et al., "Pupillary Light Reflex as an Objective Biomarker for Early Identification of Blast-Induced mTBI", J Spine, S4, 6 pages, Sep. 2013.
Centers for Disease Control and Prevention, Traumatic Brain Injury & Concussion TBI: Get the Facts, <https://www.cdc.gov/traumaticbraininjury/get_the_facts.html>, 3 pages, May 4, 2020.
Couret, D., et al., "Reliability of standard pupillometry practice in neurocritical care: an observational, double-blinded study", Critical Care, 20:99, 1-9, 2016.
Faul, M., et al., "Traumatic Brain Injury in the United States", Center for Disease Control and Prevention, <www.cdc.gov/TraumaticBrainInjury>, 74 pages, Mar. 2010.
Fischer, J., et al., "Portable Video-Oculography Device for Implementation in Sideline Concussion Assessments: A Prototype", Annu Int Conf IEEE Eng Med Biol Soc.2016, 4361-4364, 2016.
Fuhl, W., et al., "ElSe: Ellipse Selection for Robust Pupil Detection in Real-World Environments", arXiv:1511.06575v2 [cs.CV], 9 pages, Nov. 23, 2015.
Fuhl, W., et al., "ExCuSe: Robust Pupil Detection in Real-World Scenarios", Computer Analysis of Images and Patterns, Springer International Publishing, 39-51, 2015.
Fuhl, W., et al., "PupilNet: Convolutional Neural Networks for Robust Pupil Detection", arXiv:1601.04902v1 [cs.CV], 10 pages, Jan. 19, 2016.
Galetta, M., et al., "Saccades and memory: Baseline associations of the King-Devick and SCAT2 SAC tests in professional ice hockey players", Journal of the Neurological Sciences, 328, 28-31, 2013.
Galetta, K., et al., "The King-Devick test and sports-related concussion: Study of a rapid visual screening tool in a collegiate cohort", Journal of the Neurological Sciences, 309, 34-39, 2011.
Galetta, K., et al., "The King-Devick test of rapid number naming for concussion detection: meta-analysis and systematic review of the literature", Concussion, 1(2), CNC8, 15 pages, 2016.
Giardini, M., "A Smartphone Based Ophthalmoscope", Annu Int Conf IEEE Eng Med Biol Soc.2014, 4 pages, 2014.

(56) References Cited

OTHER PUBLICATIONS

Goodfellow, I., et al., "Deep Learning", MIT Press, <http://www.deeplearningbook.org>, 66 pages, 2016.

Harmon, K., et al., "American Medical Society for Sports Medicine position statement: concussion in sport", Br J Sports Med, 47, 15-26, 2013.

Kassner, M., et al., "Pupil: An Open Source Platform for Pervasive Eye Tracking and Mobile Gaze-based Interaction", arXiv:1405.0006v1 [cs.CV], 10 pages, Apr. 30, 2014.

Klingner, J., et al., "Measuring the Task-Evoked Pupillary Response with a Remote Eye Tracker", ETRA 2008, Savannah, Georgia, 69-72, Mar. 26-28, 2008.

Larson, M, et al., "Portable Infrared Pupillometry: A Review", Anesth Analg., 120(6), 1242-1253, Jun. 2015.

Larson, M, et al., "Pupillometric Analysis of the 'Absent Light Reflex'", Arch Neurol., 52, 369-372, Apr. 1995.

Lawson, E., et al., "Computational Retinal Imaging via Binocular Coupling and Indirect Illumination", SIGGRAPH 2012, Los Angeles, California, 1 page, Aug. 5-9, 2012.

Lee, H., et al., "Smartphone and tablet apps for concussion road warriors (team clinicians): a systematic review for practical users", Br J Sports Med., 49, 499-505, 2015.

Li, D., et al., "Starburst: A hybrid algorithm for video-based eye tracking combining feature-based and model-based approaches", 2005 IEEE Computer Society Conference on Computer Vision and Pattern Recognition (CVPR'05)—Workshops, San Diego, California, 1-8, 2005.

Lindsay, J., "The Significance of a Positional Nystagmus in Otoneurological Diagnosis", The Laryngoscope, 55(10), 527-551, Oct. 1945.

Long, J., et al., "Fully Convolutional Networks for Semantic Segmentation", arXiv:1411.4038v2 [cs.CV], 10 pages, Mar. 8, 2015.

Mariakakis, A., et al., "BiliScreen: Smartphone-Based Scleral Jaundice Monitoring for Liver and Pancreatic Disorders", Proceedings of the ACM on Interactive, Mobile, Wearable and Ubiquitous Technologies, 1(2), Article 20, 26 pages, Jun. 2017.

Martínez-Ricarte, F., et al., "Infrared pupillometry. Basic principles and their application in the non-invasive monitoring of neurocritical patients", Neurologia, 28(1), 41-51, 2013.

Maruta, J., et al., "A unified science of concussion", Ann. N.Y. Acad. Sci., 1208, 58-66, 2010.

Maruta, J., et al., "EYE-TRAC: monitoring attention and utility for mTBI", SPIE 8371, Sensing Technologies for Global Health, Military Medicine, Disaster Response, and Environmental Monitoring II; and Biometric Technology for Human Identification IX, 83710L, May 4, 2012, 12 pages, 2012.

Marvez, A., "Players may try to beat concussion tests", FoxSports.com, <https://www.foxsports.com/nfl/story/nfl-players-could-try-to-beat-concussion-tests-042111>, 4 pages, Apr. 21, 2011.

Mccrory, P., et al., "Consensus statement on concussion in sport: the 4th International Conference on Concussion in Sport held in Zurich, Nov. 2012", Br J Sports Med., 47, 250-258, 2013.

Meeker, M., et al., "Pupil Examination: Validity and Clinical Utility of an Automated Pupillometer", Journal of Neuroscience Nursing, 37(1), 34-40, Feb. 2005.

Morris, T., et al., "Blink detection for real-time eye tracking", Journal of Network and Computer Applications, 25, 129-143, 2002.

Moser, R.S., et al., "Neuropsychological evaluation in the diagnosis and management of sports-related concussion", Archives of Clinical Neuropsychology, 22, 909-916, 2007.

Olson, D., et al., "Interrater Reliability of Pupillary Assessments", Neurocrit Care, 24, 251-257, 2016.

Pamplona, V., et al., "NETRA: Interactive Display for Estimating Refractive Errors and Focal Range", ACM transactions on graphics (TOG), 29(4), 77, 8 pages, 2010.

Pizer, S., et al., "Adaptive Histogram Equalization and Its Variations", Computer Vision, Graphics, and Image Processing, 39, 355-368, 1987.

Rafiqi, S., et al., "PupilWare: Towards Pervasive Cognitive Load Measurement using Commodity Devices", Proceedings of the 8th ACM International Conference on PErvasive Technologies Related to Assistive Environments—PETRA '15, 9 pages, 2015.

Swirski, L., et al., "Robust real-time pupil tracking in highly off-axis images", ETRA '12: Proceedings of the Symposium on Eye Tracking Research and Applications, 4 pages, Mar. 2012.

Taylor, W., et al., "Quantitative pupillometry, a new technology: normative data and preliminary observations in patients with acute head injury", J Neurosurg, 98, 205-213, 2003.

Thiagarajan, P., et al., "Pupillary responses to light in chronic non-blast-induced mTBI", Brain Injury, 29(12), 1420-1425, 2015.

Timm, F., et al., "Accurate Eye Centre Localisation by Means of Gradients", Conference: VISAPP 2011—Proceedings of the Sixth International Conference on Computer Vision Theory and Applications, Vilamoura, Algarve, Portugal, 7 pages, Mar. 5-7, 2011.

Truong, J., et al., "Comparison of pupillary dynamics to light in the mild traumatic brain injury (mTBI) and normal populations", Brain Injury, 30(11), 1378-1389, 2016.

Truong, J., et al., "Influence of refractive error on pupillary dynamics in the normal and mild traumatic brain injury (mTBI) populations", Journal of Optometry, 11, 93-102, 2018.

Truong, J., et al., "Objective Pupillary Correlates of Photosensitivity in the Normal and Mild Traumatic Brain Injury Populations", Military Medicine, 181(10), 1382-1390, Oct. 2016.

Truong, J., et al., "Quantifying pupillary asymmetry through objective binocular pupillometry in the normal and mild traumatic brain injury (mTBI) populations", Brain Injury, 30(11), 1372-1377, 2016.

Langston, J., "PupilScreen aims to allow parents, coaches, medics to detect concussion, brain injuries with a smartphone", washington.edu, <https://washington.edu/news/2017/09/06/pupilscreen-aims-to-allow-parents-coaches-medics-to-detect-concussion-brain-injuries-with-a-smartphone/>, 7 pages, Sep. 6, 2017.

Wood, E., et al., "Eye Tab: Model-based gaze estimation on unmodified tablet computers", ETRA '14: Proceedings of the Symposium on Eye Tracking Research and Applications, 4 pages, Mar. 2014.

Zafar, S., et al., "Automated pupillometerfor monitoring the critically ill patient: A critical appraisal", Journal of Critical Care, 29, 599-603, 2014.

International Search Report and Written Opinion dated Aug. 3, 2018, issued in corresponding International Application No. PCT/US2018/035432, filed May 31, 2018, 12 pages.

* cited by examiner

SMARTPHONE-BASED DIGITAL PUPILLOMETER

CROSS-REFERENCE(S) TO RELATED APPLICATION(S)

This application is a National Stage of International Application No. PCT/US2018/035432, filed May 31, 2018 which claims the benefit of Provisional Application No. 62/513,808, filed Jun. 1, 2017, the entire disclosure of which is hereby incorporated by reference herein for all purposes.

BACKGROUND

Traumatic brain injury (TBI) accounts for 30% of all injury-related deaths in the United States. TBI can occur in a variety of situations, including car accidents, falls, and blunt force trauma. A concussion is a specific form of TBI caused by a swift blow to the head; these injuries tend not to be life-threatening, but can have serious and long-term effects on a person's memory, motor abilities, and overall cognition. One area in which concussions have garnered national attention is sports, particularly contact sports such as boxing, hockey, and American football. The Center for Disease Control (CDC) estimates that there are roughly 3.8 million concussions per year in the US, and about half of them will go undiagnosed. Patients suffering a concussion have a 600% increased risk of a future head injury and 15% increased risk of permanent cognitive deficits. This is particularly more problematic for younger athletes who are not as well-educated on concussion prevention measures such as proper tackling technique. Roughly 250,000 young Americans (<20 years old) were treated for sports-related concussions in 2009. High school football players are 3 times more likely to suffer a catastrophic head injury than college football players. Athletic departments with major funding can afford to have a team doctor with years of experience on-hand to diagnose concussions. For teams that are not as well-funded (e.g., pee-wee, middle school, high school), a school nurse, volunteer, or parent must put themselves in the same position as those doctors, but without the same tools or knowledge at their disposal. Identifying concussions immediately is essential because allowing a concussed athlete to return to play can lead to further significant injury. There exists a need for accessible concussion screening that anyone can use at any moment.

A quantitative method to assess a TBI is to check a person's pupillary light reflex (PLR), or the manner in which their pupils react to a light stimulus. The PLR of those who have suffered a TBI is typically either slower or not as pronounced. There are two methods used by clinicians to measure the PLR. The clinical gold standard method uses a device called a pupilometer that uses infrared imaging. Infrared-based pupilometry takes advantage of the fact that there is a better demarcated boundary between the pupil and the iris when infrared imaging is used. While pupil diameter is tracked using infrared light, a ring of white LEDs stimulates the eye, causing the pupillary constriction. The components needed to make a pupillometer can be inexpensive, but the total product costs ~$4,500 USD because, among other reasons, it is a self-contained system with strict hardware requirements.

A low-cost alternative for measuring the PLR involves using a penlight—a pen-sized flashlight. A penlight test is performed by directing the penlight toward and away from the patient's eye. Because the PLR is manually observed by a clinician, penlight-based pupil measurements are more likely to be inaccurate and imprecise. Larson et al. note the inability of clinicians to detect small, but clinically significant responses. Characteristics such as constriction velocity and amplitude also cannot be measured in absolute terms when using a penlight; instead of reporting a constriction velocity as 3.8 mm/s, observers can only describe the PLR as "normal," "sluggish," or "fixed." Penlight exams lack standardization as well. Clinicians purchase penlights from different companies, each with their own brightness specifications. Even if two health care providers use the same penlight, the patient may not experience the same light stimulus because of how the clinicians hold their penlights (i.e., distance and angle) or due to differences in ambient lighting conditions. Prior work has also discussed how penlight tests can lead to poor inter-observer reliability in PLR characteristics.

A normal PLR is defined as symmetric constriction or dilation of both pupils in response to a light stimulus or its absence, respectively. The pupil size must change by a non-trivial amount within a specified time frame and should change in both eyes, regardless of which eye is stimulated. For example, when a person covers one eye while the other is exposed to bright light, the pupils of both the covered and exposed eyes should constrict, producing a phenomenon known as the consensual response.

When given pupil diameter as a function of time, clinicians focus on five simpler quantitative measures: (1) Latency (ms): the time between the beginning of the light stimulus and the start of pupil constriction; (2) Constriction velocity (mm/s): the speed at which pupil constricts; reported as mean or max; (3) Constriction amplitude (mm): the difference between the maximum pupil diameter before light stimulation and minimum pupil diameter after light stimulation; (4) Constriction percentage (%): the constriction amplitude expressed as a percentage of the initial size; and (5) Dilation velocity (mm/s): the speed at which the pupil dilates; reported as mean or max.

Because the neural pathways underlying the PLR include multiple brain regions and traverse many others, it is sensitive to a variety of injuries. Our motivating use case is traumatic brain injury. When the brain shifts inside the skull, it has the potential to injure both the cranial nerves carrying signals necessary for the production of the PLR or the brain regions that process these signals.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In some embodiments, a system comprising a mobile computing device is provided. The mobile computing device comprises a camera, a light source, a display, and a non-transitory computer-readable medium. The computer-readable medium has computer-executable instructions stored thereon which, in response to execution by at least one processor of the mobile computing device, cause the mobile computing device to perform actions comprising: initiating a video recording of at least one eye of a subject; activating and deactivating the light source during the video recording; ending the video recording; using a machine learning model to process the video recording to generate at least one dilation curve for the at least one eye; and presenting the at least one dilation curve on the display.

In some embodiments, a computer-implemented method of measuring changes in a size of a pupil over time in response to a light stimulus is provided. The computing device receives a video recording of an eye of a subject, wherein the video recording was recorded by a visible light camera. The computing device uses a machine learning model to detect changes in the size of a pupil of the eye during the video recording. The computing device provides the detected changes in the size of the pupil for presentation on a display. In some embodiments, a non-transitory computer-readable medium having computer-executable instructions stored thereon is provided. The instructions, in response to execution by one or more processors of a computing device, cause the computing device to perform such a method. In some embodiments, a computing device configured to perform such a method is provided.

In some embodiments, a computer-implemented method of generating and using a machine learning model to measure pupillary response for diagnosis of brain injury is provided. One or more mobile computing devices collect training data comprising video recordings of eyes responding to light stimuli. At least one computing devices receive tagging information indicating a location and a size of pupils in frames of each video recording. At least one computing device uses the training data and the tagging information to train a machine learning model to recognize pupil location and size in video frames. The machine learning model is stored on a mobile computing device. In some embodiments, a non-transitory computer-readable medium having computer-executable instructions stored thereon is provided. The instructions, in response to execution by one or more processors of a computing device, cause the computing device to perform such a method. In some embodiments, a computing device configured to perform such a method is provided.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 1:
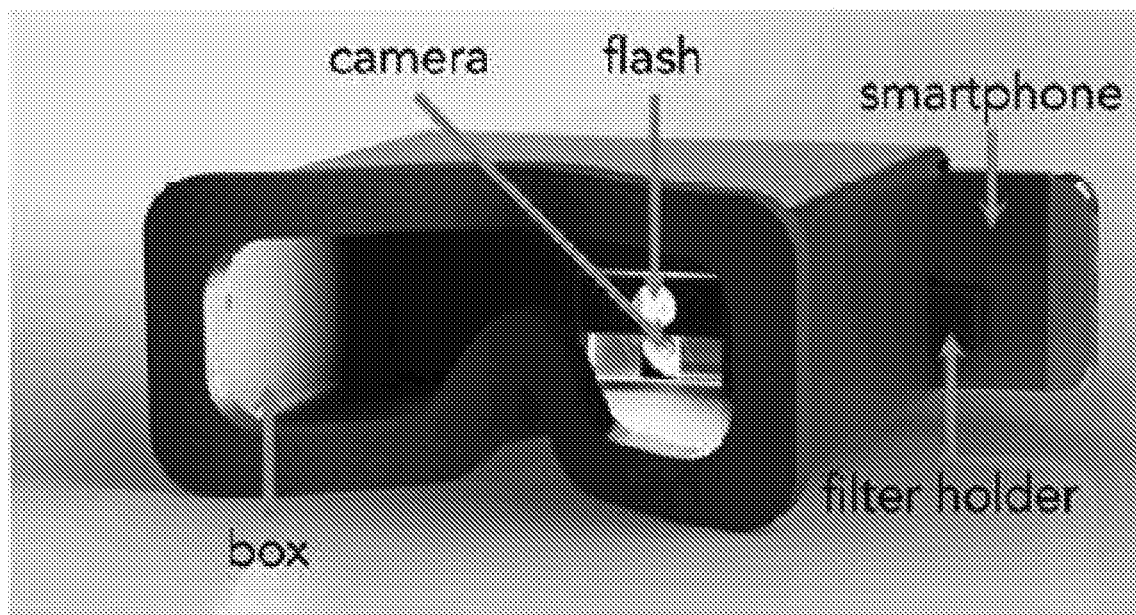
FIG. 1 illustrates an example embodiment of a box used according to various aspects of the present disclosure.

Before a person suffering from a traumatic brain injury reaches a medical facility, measuring their pupillary light reflex (PLR) is one of the few quantitative measures a clinician can use to predict their outcome. In some embodiments of the present disclosure, an application for execution on a mobile computing device (such as a smartphone app) and a box for holding the mobile computing device in relation to a face of a subject combines the repeatability, accuracy, and precision of a traditional infrared pupilometer device with the ubiquity and convenience of the penlight test that clinicians regularly use in emergency situations. The application, referred to at some points herein as "PupilScreen," stimulates the patient's eyes using the smartphone's flash and records the response using the camera. The PupilScreen box, akin to a head-mounted virtual reality display, controls the eyes' exposure to light. The recorded video is processed using machine learning models such as convolutional neural networks that determine the pupil diameter over time, allowing for the derivation of clinically relevant measures. Using a fully convolutional network, the pupil diameter was tracked with a median error of 0.30 mm. Clinical evaluations of the PupilScreen app and techniques disclosed herein demonstrated high fidelity of correct determinations in segregating healthy and unhealthy PLRs.

In some embodiments, the PupilScreen system comprises two easily obtainable components: a smartphone app and a box. Smartphones are widely available, and the box can be easily created and may not require any wiring or expensive components. This means that PupilScreen can be made available to almost anyone. The box simultaneously eliminates ambient lighting conditions and controls the distance between the person's face and the flash/camera so that pixel sizes may be reliably converted into absolute measurement sizes. In some embodiments, instead of a box, a box-like or eyeglasses-like or other type of accessory can be used. The accessory can be foldable and attachable to and detachable from the smartphone. The accessory may be inconspicuous and space saving, and easy to carry around. When attached to the smartphone, the accessory performs same functions as the box, by keeping the distance of the camera from the pupil constant and blocking ambient lighting.

In some embodiments, the PupilScreen system may not use a box or an accessory, and may instead use other techniques for dealing with ambient lighting conditions. For example, in some embodiments, the PupilScreen app may instruct the user to turn off or turn down the lights in a room in order to establish a low-level of ambient light. As another example, in some embodiments, the effects of ambient light may be dwarfed by the PLR in response to the flash, and may therefore be ignored. As still another example, data from an ambient light sensor on the smartphone may be used as an additional input to the machine learning model, and/or may be used to adjust the brightness and/or contrast of the generated video recordings to match training data.

Also, in some embodiments, the PupilScreen system may use other techniques instead of the box for determining or compensating for a distance between the person's face and the flash/camera. For example, in some embodiments, the PupilScreen system may have the subject hold an object of known size, such as an ID card, drivers' license, coin, etc., next to the eye to be measured. The known size object can then be used to convert pixel sizes into actual sizes for each frame. As another example, in some embodiments, the Pupil Screen system may use a depth sensor associated with the camera in order to determine the distance of the phone from the eye. As another example, in some embodiments, the PupilScreen system may consider pupil sizes in respect to a percentage of a size of an iris, or a percentage of a size of an eye, instead of generating absolute measurement values.

PupilScreen can track pupil diameter with a median error of 0.30 mm with the fully convolutional network. Pupil Screen can track the pupil center with a median error of 0.20 mm. Using information about the pupil diameter over time, PupilScreen extracts clinically relevant measurements, including constriction amplitude, percentage, and velocity. PupilScreen can estimate constriction amplitude with a mean absolute error of 0.62 mm for a range of amplitudes of 0.32-6.02 mm, constriction percentage with a mean absolute error of 6.43% for a range of 6.21-62.00%, and max constriction velocity with a mean absolute error of 1.78 mm/s for a range of 1.37-8.99 mm/s.

In designing a smartphone-based pupilometry system, the challenges include (1) designing a controlled setup that is portable and inexpensive, and (2) accurately identifying the pupils in video using only visible light. The PupilScreen system and method allow a smartphone to achieve repeatable PLR results at a fraction of the cost of a clinical device.

FIG. 1 illustrates an example embodiment of a box used according to various aspects of the present disclosure. The smartphone is placed into a slot in the back of the box. The box-phone combination serves several purposes, including: (1) the box controls the position of the phone relative to the person's face, including the distance to and alignment with the face, (2) the box eliminates the effects of ambient lighting conditions, and (3) the phone provides its own lighting within the box using a flash, which is incorporated into the smartphone. The dimensions of the box are determined such that the smartphone is held reliably in place, and the camera is centered within box. Having the camera close to the participant's face increases the effective resolution of their eyes, which allows PupilScreen to detect smaller changes in pupil diameter and measure the PLR with increased precision, but moving the phone further away allows the camera to see both eyes at once and reduces the discomfort caused by the intense flash.

In some embodiments, the box may be 3D-printed for durability and ease of distribution. In some embodiments, the box may be made of an even cheaper material like cardboard in order to further reduce the cost. Also note that there is no electronic connection between the phone and the box, simplifying its manufacturing requirements. To make the light more tolerable to the subject, a neutral density filter and diffuser were placed directly in front of the flash using a sliding stick.

Different network architectures can be applied. In one embodiment, the architecture is similar to PupilNet in that it involves two CNNs in sequence. However, instead of using the second network to provide a more precise estimate of the pupil center, the second network is used to estimate the pupil diameter. In this example, the first network provides a coarse estimate of the pupil center with sufficient accuracy. The second architecture is an implementation of FCN-8, a fully-convolutional neural network for achieving pixelwise segmentation.

Figure 2A:
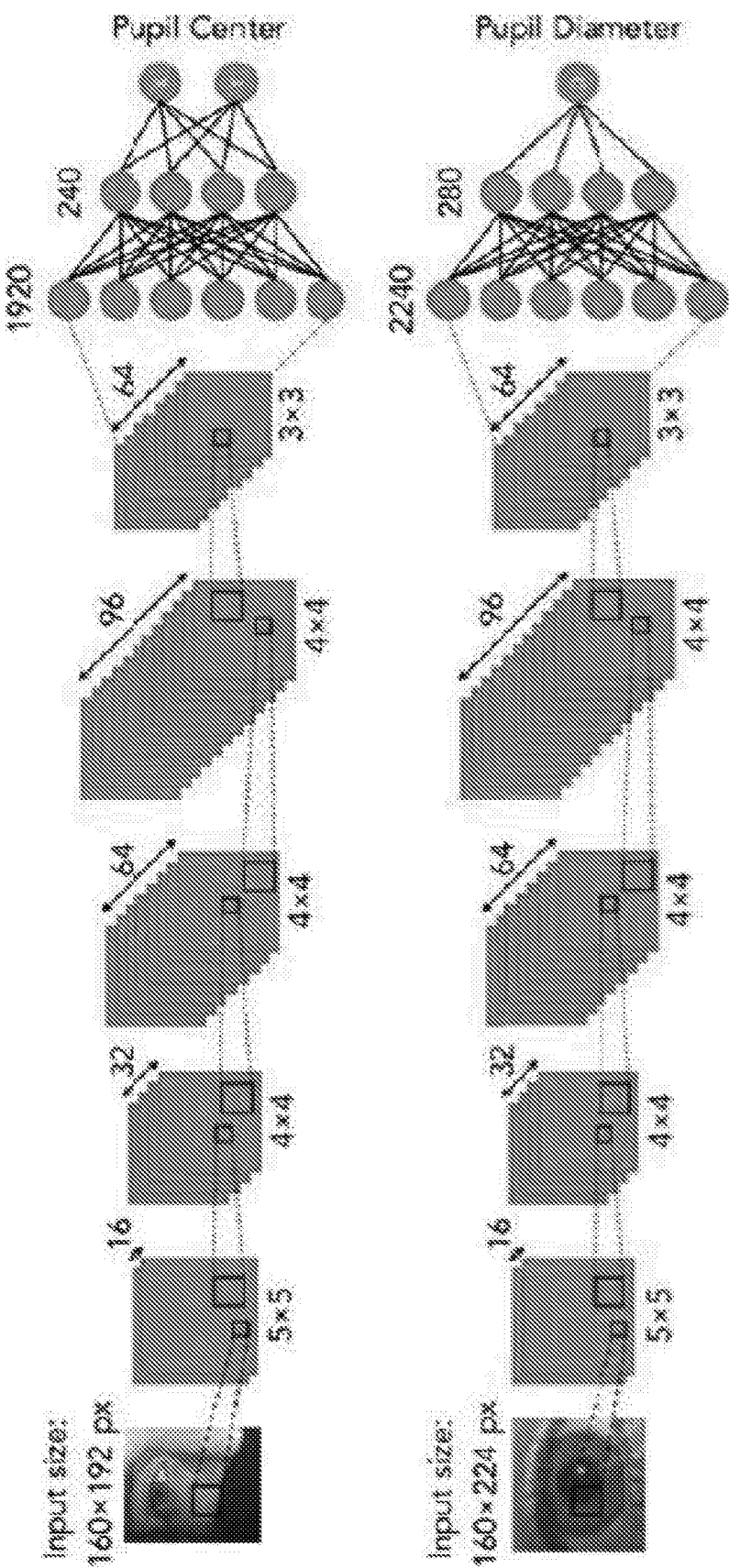
FIG. 2A illustrates an example embodiment of a convolutional neural network architecture suitable for use according to various aspects of the present disclosure.

FIG. 2A illustrates an example embodiment of a convolutional neural network architecture suitable for use according to various aspects of the present disclosure. The first network is trained to estimate the pupil center location. The second network is trained to learn the pupil diameter. Even if the pupil is not exactly centered using the output of the first network, the second network can be robust enough to handle those issues.

FIG. 2A illustrates the details of the first architecture. In this example, the first network (top) is trained to accept an image from the pre-processing step as input and return the location of the pupil center. Before being input to the network, the image is downsampled by a factor of 4. The network has 5 convolutional layers, each with a rectified linear (ReLU) activation function followed by 2×2 pixel mean-pooling layers. The final layer of the first network is fully connected to compress information across all filters and sub-regions to an x- and y-coordinate estimate. The output labels are normalized according to the mean and standard deviation of the pupil location across the entire dataset. This is done to ensure that the same error in either direction would equally affect the network's weights during backpropagation.

Using the output of the first network, a region of interest that is roughly ⅛th of the original image's size is cropped and centered about the estimated pupil. That region is provided to the second network (bottom), which is trained to estimate the pupil diameter. The network has a similar architecture to the first one except for the fact that it produces a single output: the pupil diameter.

The number of layers was determined empirically to balance the tradeoff between network size and accuracy. Smaller networks are desirable so that they can fit more easily on the smartphone, but may yield less satisfactory results.

Figure 2B:
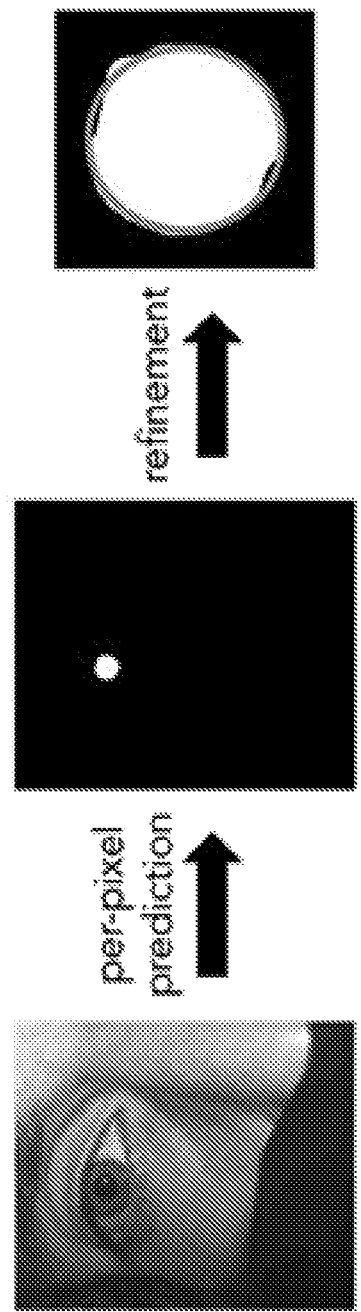
FIG. 2B illustrates another example embodiment of a convolutional neural network architecture suitable for use according to various aspects of the present disclosure.

FIG. 2B illustrates another example embodiment of a convolutional neural network architecture suitable for use according to various aspects of the present disclosure. In this fully convolutional architecture, the first network architecture learns the pixel indices of the pupil center and the diameter of the pupil, but treats them just like any other continuous outputs rather than explicit location and size information. The second network architecture takes a different approach, viewing the problem as one of explicit segmentation. The goal of segmentation is to produce a label for every single pixel that specifies the object to which it belongs. As illustrated in FIG. 2B, there are two classes for the purposes of PupilScreen: "pupil" and "non-pupil". Implemented in this example is FCN-8, a fully convolutional architecture. In short, fully convolutional networks are normally based on a pre-trained convolutional network for image classification (e.g., VGG16). The final classifier layer is removed and replaced by layers that deconvolve, or upsample, the downsampled predictions to their original resolution. For the sake of network size, images can be downsampled by a factor of 2 before inputting them to the network.

Once pixelwise predictions are produced, there is still the matter of measuring a pupil diameter. The largest contiguous cluster of pixels with the "pupil" label is treated as the pupil. The border of that cluster is smoothed using median blurring and then fit to an ellipse. The mean of the ellipse's two axes is treated as the pupil diameter for that frame.

Figure 3:
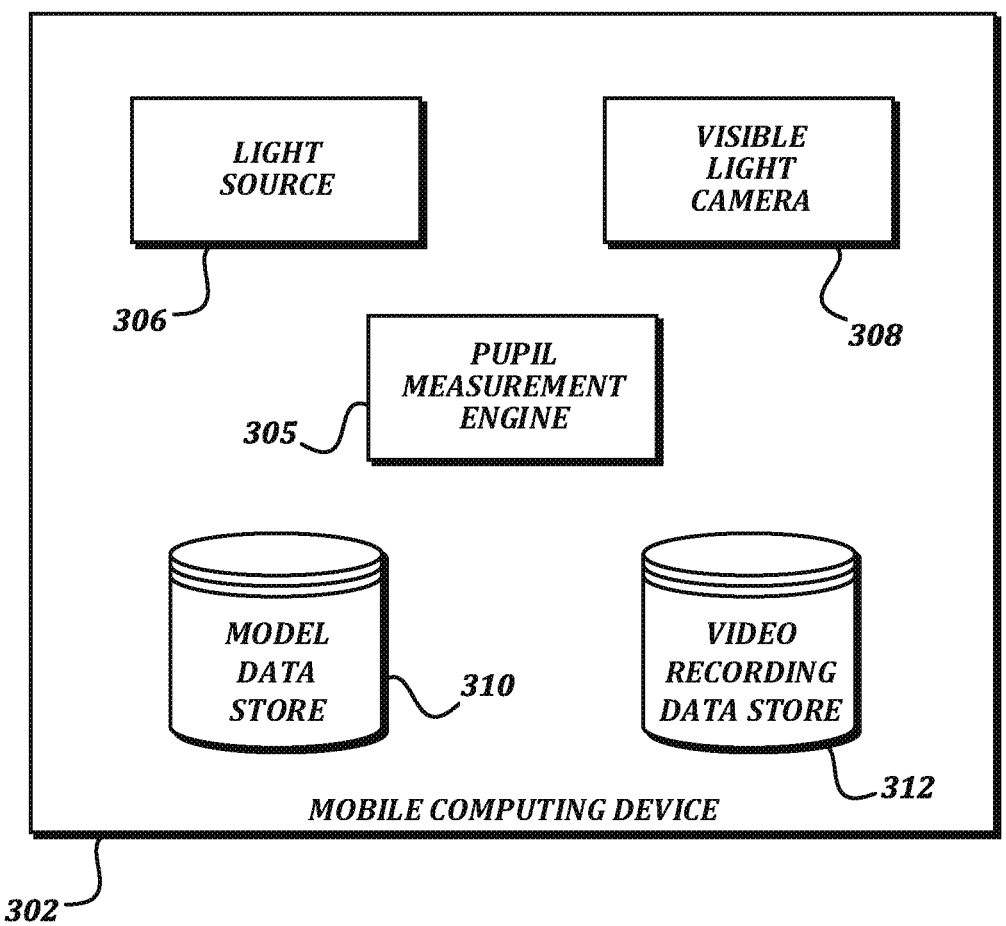
FIG. 3 is a block diagram that illustrates an example embodiment of a mobile computing device and a training computing device according to various aspects of the present disclosure.
Figure 3:
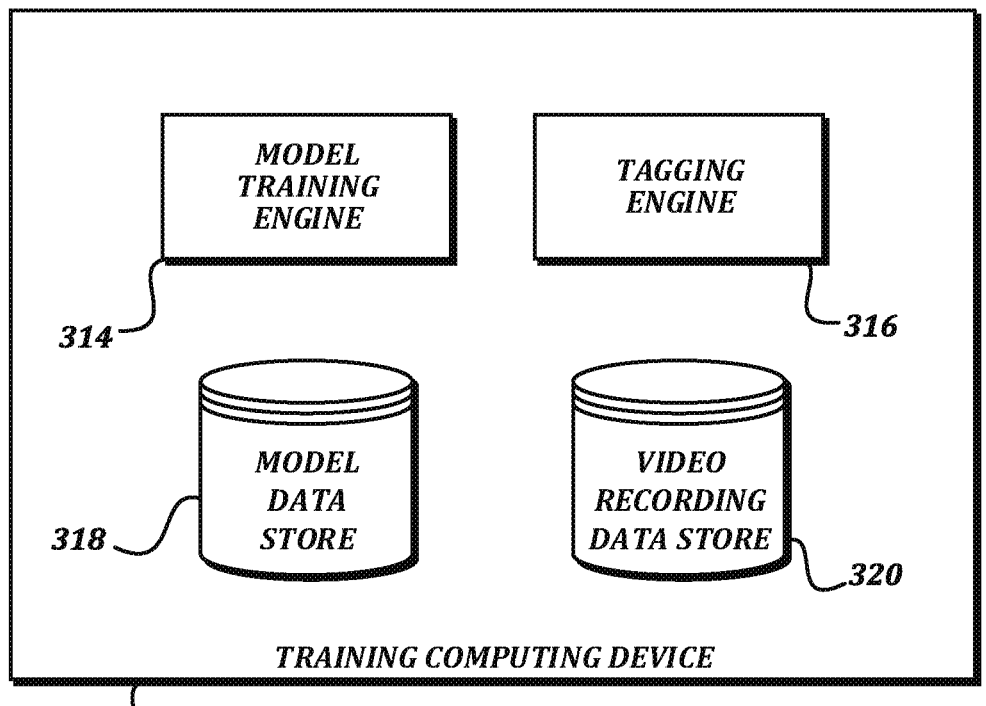

FIG. 3 is a block diagram that illustrates an example embodiment of a mobile computing device 302 and a training computing device 304 according to various aspects of the present disclosure. In some embodiments, the mobile computing device 302 is a smartphone such as an iPhone, an Android phone, or any other mobile computing device having the illustrated features. In some embodiments that do not use a box, any computing device having the illustrated features (such as a light source 306 and a visible light camera 308), including but not limited to tablet computing devices, laptop computing devices, and desktop computing devices, may be used as the mobile computing device 302.

In some embodiments, the training computing device 304 may also be a smartphone. In some embodiments, the training computing device 304 may be a desktop computing device, server computing device, or cloud computing device that processes video recordings generated by mobile computing devices. In some embodiments, the mobile computing device 302 and the training computing device 304 may be the same computing device, or at least the same type of computing device. In some embodiments, the mobile computing device 302 and the training computing device 304 may be separate devices that communicate with each other (and/or other devices) via any suitable networking technology. In some embodiments, the training computing device 304 may create machine learning models, and the models may be transmitted to the mobile computing device 302 as part of an app download from an app store.

As shown, the mobile computing device 302 includes a light source 306, a visible light camera 308, a pupil measurement engine 305, a model data store 310, and a video recording data store 312. In some embodiments, the light source 306 is a source of visible light, such as an LED flash (or a flash that uses another technology) intended to provide light for taking pictures with the mobile computing device 302. In some embodiments, the visible light camera 308 includes a CMOS image sensor and is configured to generate digital video information. Digital cameras configured to record videos and light sources are common components installed on mobile computing devices 302 such as smartphones, and so are not described further herein for the sake of brevity.

In some embodiments, the pupil measurement engine 305 is configured to cause a video recording to be generated and stored in the video recording data store 310. In some embodiments, the pupil measurement engine 305 may also be configured to process the video recording using a machine learning model stored in the model data store 310 in order to measure the size over time of one or more pupils in the video recording, and may be configured to provide indications of the size over time for presentation on a display. Further description of the actions performed by the pupil measurement engine 305, model data store 310, and video recording data store 312 is provided below.

As shown, the training computing device 304 includes a model training engine 314, a tagging engine 316, a model data store 318, and a video recording data store 320. In some embodiments, the model training engine 314 may be configured to cause video recordings to be created for training, and/or may be configured to receive video recordings recorded by another device, and to have the recordings stored in the video recording data store 320. In some embodiments, the tagging engine 316 is configured to cause pixels in frames of the video recordings to be tagged as either belonging to a pupil or not belonging to a pupil, and to store the tagging information along with the video recordings. Then, the model training engine 314 uses the tagging information and the video recordings to train machine learning models and to store the trained models in the model data store 318. Further description of the actions performed by the model training engine 314, the tagging engine 316, the model data store 318, and the video recording data store 320 is provided below.

In general, the word "engine," as used herein, refers to logic embodied in hardware or software instructions, which can be written in a programming language, such as C, C++, COBOL, JAVA™, PHP, Perl, HTML, CSS, JavaScript, VBScript, ASPX, Microsoft .NET™, Objective-C, Swift, MATLAB, and/or the like. An engine may be compiled into executable programs or written in interpreted programming languages. Software engines may be callable from other engines or from themselves. Generally, the engines described herein refer to logical divisions of functionality that can be merged with other engines, or can be divided into sub-engines. The engines can be stored in any type of computer-readable medium or computer storage device and be stored on and executed by one or more general purpose computers, thus creating a special purpose computer configured to provide the engine.

In general, the term "data store," as used herein, refers to any device that stores information on a non-transitory computer readable medium such as a magnetic drive, RAM, ROM, flash memory, and/or the like, in an organized manner. As a non-limiting example, a data store may store data within files in a file system. As more non-limiting examples, a data store may store data in a manner intended to provide high reliability, indexing, searching, and retrieval, including but not limited to a relational database management system (RDBMS), a key-value store, an object store, and/or the like.

Figure 4:
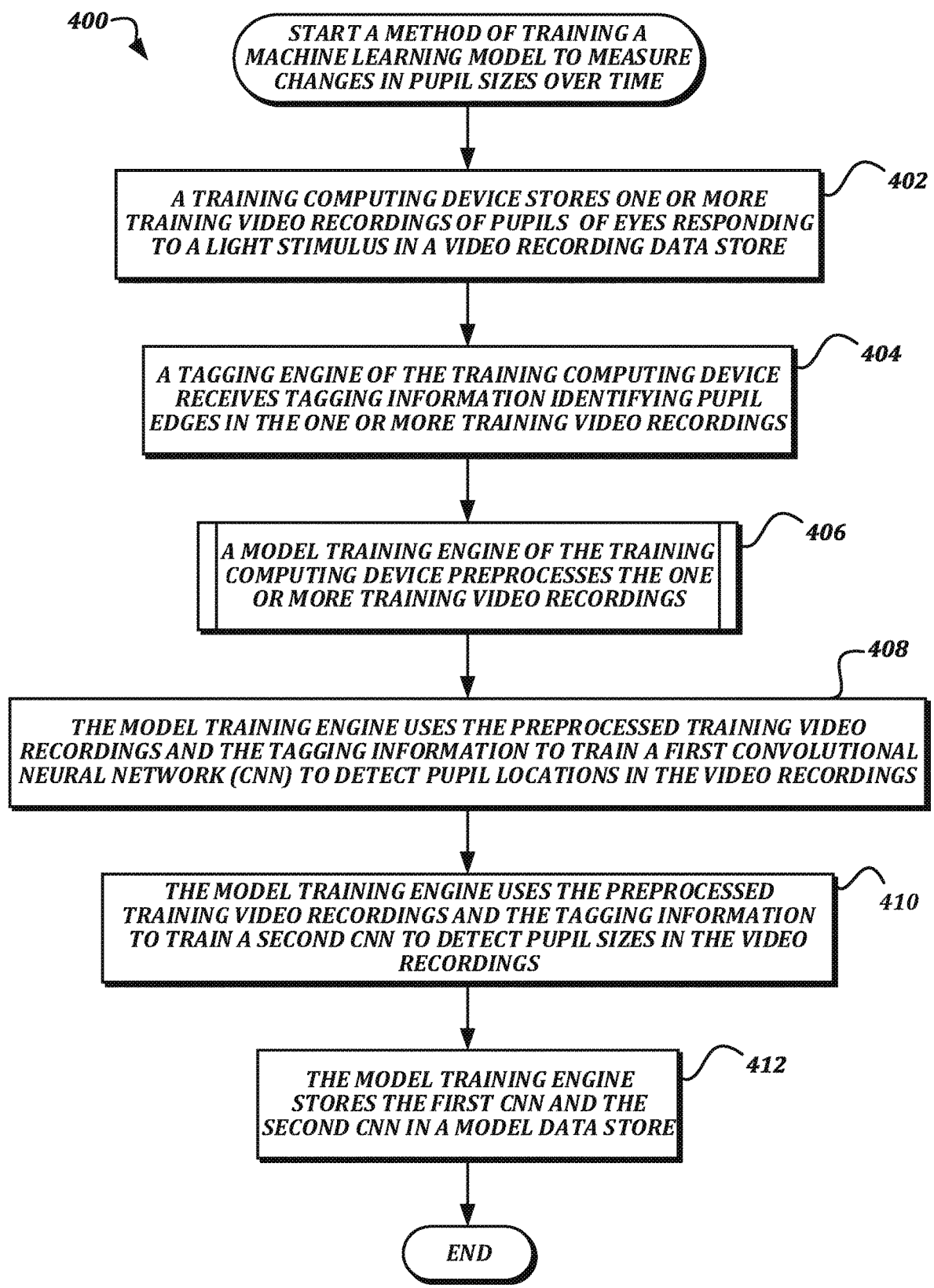
FIG. 4 is a flowchart that illustrates an example embodiment of a method of training a machine learning model to measure changes in pupil sizes over time according to various aspects of the present disclosure.

FIG. 4 is a flowchart that illustrates an example embodiment of a method of training a machine learning model to measure changes in pupil sizes over time according to various aspects of the present disclosure. From a start block, the method 400 proceeds to block 402, where a training computing device 304 stores one or more training video recordings of pupils of eyes responding to a light stimulus in a video recording data store 320. In some embodiments, the video recordings may be created by the training computing device 304 itself, if it is a smartphone that is similar to the mobile computing device 302 to be used during testing. In some embodiments, the training video recordings may be created by the mobile computing device 302, and transmitted to the training computing device 304 for training.

An example embodiment of the recording of a training video recording, which was used in testing an embodiment of the present disclosure, is as follows: Prior to putting the box up to their face, participants were asked to take off glasses if they wore them. Once the phone was placed in the box and the participant held it up to their face, the flash was turned on briefly and autofocus was enabled. The resulting camera focus was fixed for the remainder of the study to avoid blurriness as the lighting in the box changed. The flash was then turned off and after a brief pause to allow the pupils to recover, data collection commenced. The video recording was recorded at 30 fps with 1920×1080 resolution. After an audible 3-second countdown from the phone's speakers, the flash illuminated the participant's eyes. The stark change in lighting maximized the degree to which the pupil constricted, akin to the difference experienced when using a pupilometer. The recording stayed on for another five seconds, resulting in an 8-second long recording. The five second period after the introduction of the light stimulus was far longer than what was needed to capture the PLR, but provided extra video frames for evaluation. For each study participant, the PLR was recorded three times. Between recordings, a one-minute break was added to allow the participant to rest their eyes.

Next, at block 404, a tagging engine 316 of the training computing device 304 receives tagging information identifying pupil edges in the one or more training video recordings. In some embodiments, the tagging engine 316 may cause a user interface to be presented that allows a human operator to generate tagging information by labeling pixels within frames of the training video recordings as being either within a pupil or outside of a pupil. In some embodiments, the tagging information may be stored along with the training video recordings in the video recording data store 320.

Figure 5:
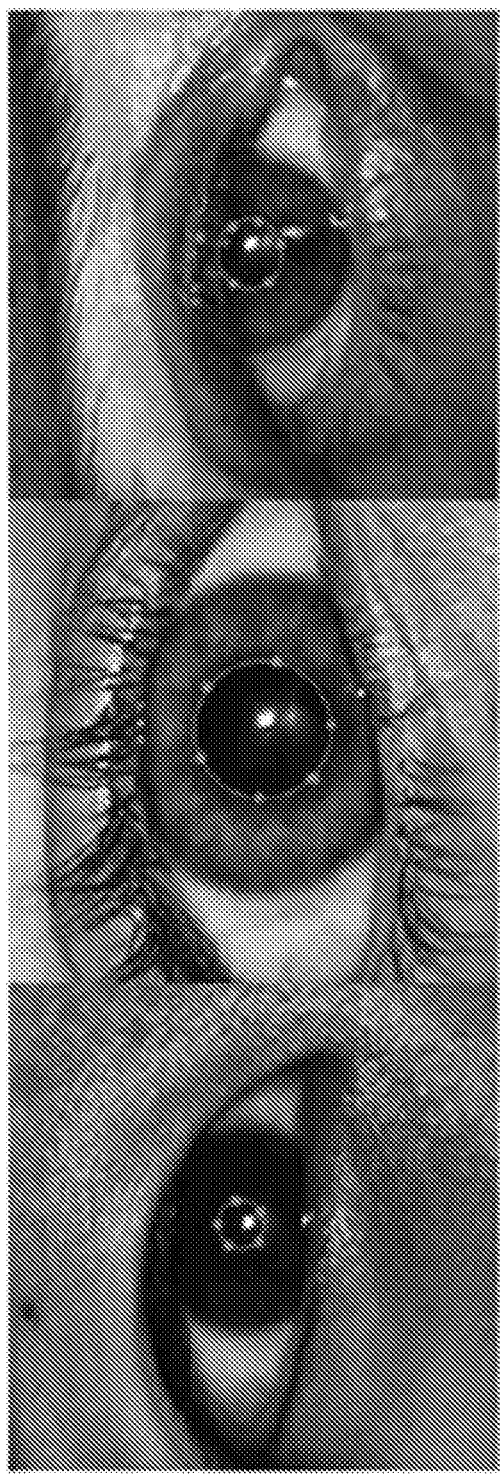
FIG. 5 illustrates three examples of labels created by researchers on training video recordings according to various aspects of the present disclosure.

An example embodiment of the collection of tagging information, which was used in testing an embodiment of the present disclosure, is as follows: Video recordings were manually annotated to generate ground truth labels. Using the tagging engine 316, two researchers labeled frames by selecting points along the edges of the pupils and letting OpenCV's ellipse fitting algorithm generate a corresponding outline. FIG. 5 illustrates three examples of the labels created by the researchers. The researchers could see and adjust the outlines to better fit the images. If the pupil was difficult to distinguish from the iris, the researchers could adjust the contrast to make it more visible. If the pupil was still too difficult to see after that, either because of poor focus or lighting, the frame was skipped; this only happened for 1.8% of the total frames encountered. The points were fit to an ellipse because not all pupils are circular. Since pupilometry is only concerned with a single pupil diameter, the ellipses were converted to circles by averaging their axes. With this method, the pupil diameters were labeled in pixels. The researchers labeled every fifth frame in the three videos from each user. Each video was 8 seconds long, but the first 3 seconds occur before the flash was turned on, resulting in 5 seconds×30 frames/second×(⅕ frames)×3 videos=90 labeled frames per person. Frames were labeled independently of one another to avoid biases between frames; however, this led to greater variation between consecutive frames that can be primarily attributed to human error. A 3rd-order Savitzky-Golay filter was applied to temporally smooth the pupil center and diameter labels. To quantify the agreement of the labels across the researchers, both labeled a common set of 5 users (15 videos, 450 frames). The average difference between the smoothed pupil center labels was 3.46 px, which translates to 0.27 mm. The average difference between the smoothed pupil diameter labels was 2.00 px, which translates to 0.16 mm. Note that these variations are not independent; if a researcher underestimated the extent of an edge, the labeled center would move away from that edge and the labeled diameter would be lower than the actual value. The degree of inter-researcher agreement can also be quantified using the intersection-over-union (IoU) measure, a standard metric for segmentation agreement between two regions. The mean IoU for the researchers' labels was 83.0%. Note that the IoU measure is calculated relative to the total area of the two labeled pupils. If the pupil center labels for a 3 mm pupil were only off by a single pixel, that difference alone would lead to an IoU score of 93.8%.

Handling different gaze directions is a simple matter when using this technique. If the ellipse's eccentricity is too low (e.g., its axes are uneven), the frame may be rejected. Frames with a blink may similarly be rejected. Instead of averaging the axes to determine a circle, the maximum of the ellipse's axes could have been used since the dimension parallel to the direction of the rotation decreases in size; however, we chose to use the mean as a compromise between this phenomenon and the fact that some pupils have small protrusions along their perimeter that artificially extend their clinically significant boundary.

Although a clinical-grade pupillometer could have provided an alternative method for quantifying the PLR, its results would not have been directly comparable to PupilScreen. The two setups have light stimuli with different intensities, which would result in different magnitudes of pupil constriction. Furthermore, PupilScreen eliminates the effect of ambient lighting because the box completely encloses the patient's eyes, whereas pupillometers do not since they are used in hospitals with roughly standard lighting conditions. Infrared imaging could have been used to provide a comparative ground truth measurement of pupil diameter; however, an algorithm still would have been needed to turn those frames into pupil diameters, and that algorithm would have needed its own validation.

At procedure block 406, the model training engine 314 of the training computing device 304 conducts a procedure that preprocesses the one or more training video recordings. An input to the procedure is one or more training video recordings, and an output of the procedure is a result of the preprocessing (e.g., one or more preprocessed video recordings). Any suitable procedure may be used for preprocessing. In general, the goals of preprocessing may be to improve contrast; to reduce data to be analyzed without unduly affecting accuracy; and so on. In some embodiments, preprocessing may include segmenting the video recording so that only a single eye/pupil is included in each video (so a video of both pupils would be split into two), or may flip video recordings so that all of the eyes are oriented in the same direction (e.g., the video recordings are flipped so that the medial canthus is on the right side of the video recording whether it depicts a left eye or a right eye). In some embodiments, preprocessing may produce additional training data, such as by jittering the video recordings. An example of a procedure suitable for use for preprocessing is described in detail below.

Next, at block 408, the model training engine 314 uses the preprocessed training video recordings and the tagging information to train a first convolutional neural network (CNN) to detect pupil locations in the video recordings. The method 400 then proceeds to block 410, where the model training engine 314 uses the preprocessed training video recordings and the tagging information to train a second CNN to detect pupil sizes in the video recordings. In some embodiments, the pupil sizes and pupil locations may be indicated in absolute size (e.g., millimeters). In some embodiments, the pupil sizes and pupil locations may be indicated in pixels that could be converted to millimeters. In some embodiments, the pupil sizes and pupil locations may be indicated in percentages of total eye size (and therefore be independent of distance from the camera 308).

Both architectures were trained with backpropagation using batches composed of 10 images randomly sampled from the training set. To ensure that there was no overlap between training and testing data, the evaluation was conducted using 5-fold cross-validation across users; in other words, if there are N users, N/5 users are held out each time for testing and the remaining 4×N/5 users are used for training. Recall that three videos were recorded for each user. All networks were trained for 10 epochs per fold; this number was determined empirically based on the convergence of the smoothed loss function outputs across the training data. On average, training the first network architecture took 14 mins per fold, resulting in a total training time of 14 mins×5 folds×2 networks=2 hours 20 mins. Training the second network architecture took 1 hours 59 mins per fold, resulting in a total training time of 119 mins×5 folds=9 hours 55 mins. Computation was carried out by a single NVidia GeForce Titan X GPU. Testing an individual frame through either network architecture took approximately 2 ms, which means that it would take the system roughly 2 ms×30 frame/second×5 seconds=300 ms to test an entire video. The networks in the sequential CNN architecture were trained using batch gradient descent in order to minimize the L2 loss. The fully convolutional network was trained in the same way to minimize the per-pixel multinomial logistic loss.

To ensure that the dataset was not significantly biased towards images of fully constricted pupils, only frames within the first 3 seconds of the light stimulus were used for training. To both generate more training samples and further promote training data diversity, training images and their associated labels were randomly jittered together (i.e., translated by a small amount). That amount was at most 10% of the input image dimensions for the first network, which was determined based on the variation of the pupil center observed in the videos. The jitter amount was at most 15% of the input image dimensions for the second network in order to sufficiently cover the spread of pupil center predictions from the first network. In this latter case, jittering the input images allows the second network to be trained to tolerate such errors.

At block 412, the model training engine 314 stores the first CNN and the second CNN in a model data store 318. The method 400 then proceeds to an end block and terminates.

Figure 6:
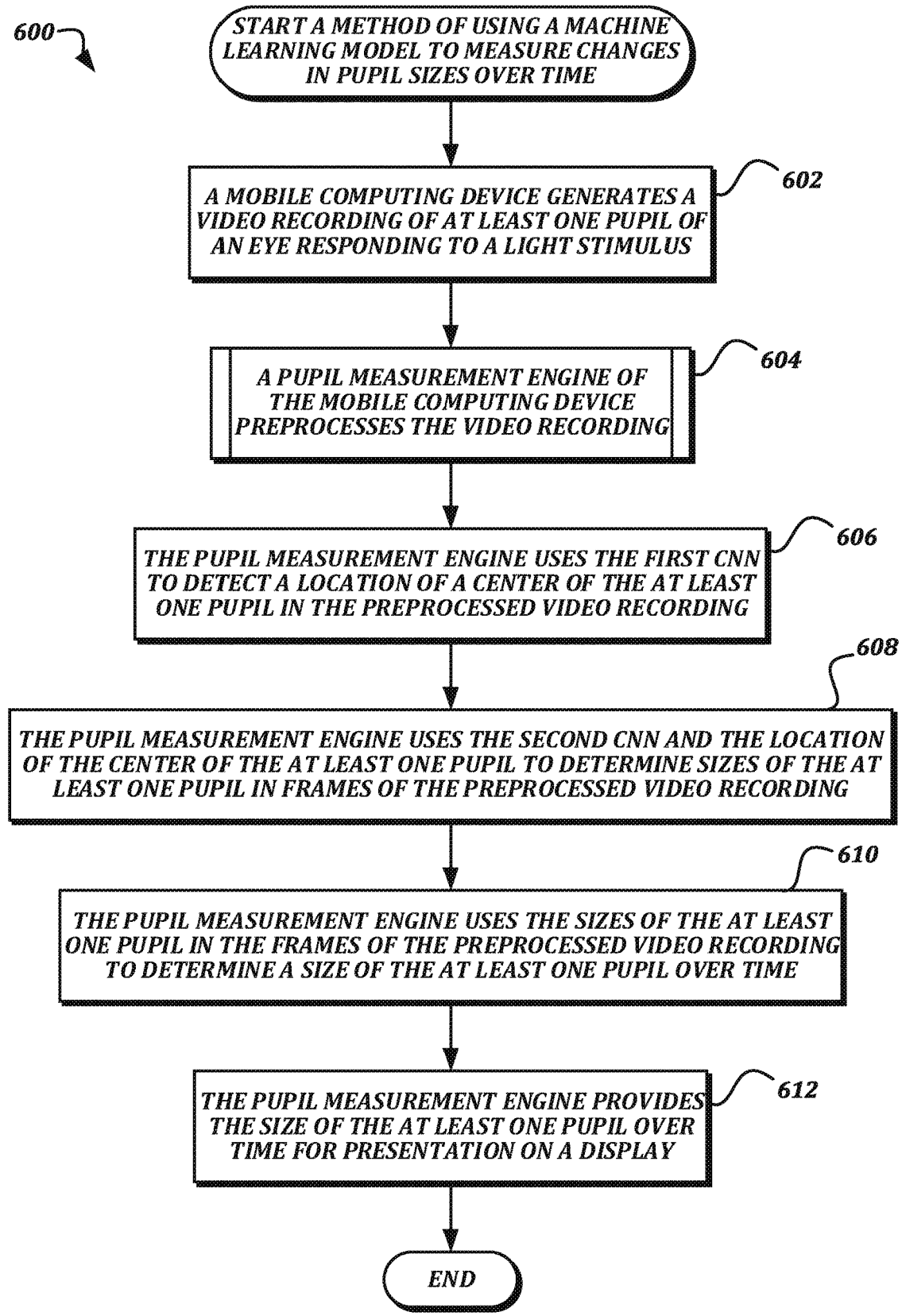
FIG. 6 is a flowchart that illustrates an example embodiment of a method of using a machine learning model to measure changes in pupil sizes over time according to various aspects of the present disclosure.

FIG. 6 is a flowchart that illustrates an example embodiment of a method of using a machine learning model to measure changes in pupil sizes over time according to various aspects of the present disclosure. From a start block, the method 600 proceeds to block 602, where a mobile computing device 302 generates a video recording of at least one pupil of an eye responding to a light stimulus. In some embodiments, the video recording may be stored in the video recording data store 312. The video recording is of at least one pupil because in some embodiments, a single eye may be in the field of view of the camera 308, while in other embodiments, both eyes may be in the field of view of the camera 308. In some embodiments, the video recording is generated using a technique that matches the technique used to generate the training videos so that the machine learning model will be able to properly interpret the information. Accordingly, if the training videos were generated using a box, the video recording at block 602 is also generated using a box. In some embodiments, the mobile computing device 302 used at block 602 is the same type of computing device used to record the training videos. For example, both computing devices may be iPhone 7 smartphones.

At procedure block 604, a pupil measurement engine 305 of the mobile computing device conducts a procedure that preprocesses the video recording. An input to the procedure is the video recording, and an output of the procedure is a result of the preprocessing (e.g., one or more preprocessed video recordings). Any suitable procedure may be used for preprocessing. Typically, a procedure that matches the procedure used at procedure block 406 of FIG. 4 is used so that the preprocessed video recording matches the preprocessed video recordings used to train the machine learning model. An example of a procedure suitable for use for preprocessing is described in detail below.

The method 600 then proceeds to block 606, where the pupil measurement engine 305 uses the first CNN to detect a location of a center of the at least one pupil in the preprocessed video recording. The first CNN may be stored in the model data store 310, and may have been generated by the method 400 described above. In some embodiments, the first CNN processes the preprocessed video recording frame-by-frame to determine pupil locations in the frames. In some embodiments, a sampling of frames may be processed instead of processing every frame in the preprocessed video recording. In some embodiment, the pupil measurement engine 305 stores the location of the center of the at least one pupil along with each frame of the preprocessed video recording.

Next, at block 608, the pupil measurement engine 305 uses the second CNN and the location of the center of the at least one pupil to determine sizes of the at least one pupil in frames of the preprocessed video recording. In the sequential embodiments, the location of the center of the at least one pupil is used to crop a portion of the frames that is likely to include the pupil, such as the $\frac{1}{9}^{th}$ portion of the frame as illustrated in FIG. 2A. In the fully convolved embodiments, this may occur as well, or the output of the first CNN may be used as a continuous input to the second CNN. The second CNN may also be stored in the model data store 310, and may have been generated by the method 400 described above. Again, the technique of block 608 may process the video recording frame by frame, using the pupil location stored for each frame, and again the technique may process either every frame or a subset of frames.

At block 610, the pupil measurement engine 305 uses the sizes of the at least one pupil in the frames of the preprocessed video recording to determine a size of the at least one pupil over time. In some embodiments, the pupil measurement engine 305 may store the sizes as a time series. In some embodiments, the pupil measurement engine 305 may generate a graph or chart based on the time series. In some embodiments, the pupil measurement engine 305 may convert units for the sizes.

A PLR curve such as the graphs or charts that may be generated by the pupil measurement engine 305 shows a patient's pupil diameter as a function of time following a light stimulus. In some embodiments, the pupil measurement engine 305 may perform one or more post-processing steps to make the resulting curve more comparable to the curves provided by pupilometers, including but not limited to: (1) removing extreme prediction outliers using heuristics based on human physiology: pupils should not be smaller than 1 mm or larger than 10 mm, and the pupil diameter should not change by more than 10 mm/s; (2) smoothing the predictions (like the ground truth labels) using a 3rd-order Savitzky-Golay filter to remove undesirable fluctuations between frames that occur because the pupil diameter is estimated from each frame individually; and/or (3) scaling predictions from pixels to millimeters using a constant factor that was estimated through a device calibration procedure. A fiducial of known dimensions was placed in front of the camera at roughly the same distance as the user's eyes; its dimensions were measured in pixels and the calculated ratio was applied to all videos. This approach is not perfect since different people have different eye socket depths. Nevertheless, the ground truth labels used for analyses are all in pixels, so the conversion is primarily used to transform the results into more relevant units.

Relevant clinical measures as described above can be extracted from the smoothed and scaled PLR curve. Calculations for the constriction amplitude and the constriction percentage may use the minimum and maximum pupil diameter. The maximum pupil diameter typically occurs at the beginning of the video since the pupil is most dilated before the light stimulus. After the pupil constricts, its diameter can fluctuate as it reaches its final equilibrium size. Because of this, the minimum diameter is identified by taking the average diameter in the last second. The maximum constriction velocity is calculated by computing the maximum of the centered derivatives across the entire curve. Although PupilScreen is designed to measure the latency between the time of the light stimulus and when the pupil begins to constrict, we found that the frame rate used may limit the granularity of the calculation $((30 \text{ fps})^{-1}=0.03$ s/frame). If the latency is desired, higher frame rates may be used.

At block 612, the pupil measurement engine 305 provides the size of the at least one pupil over time for presentation on a display. The display may be a display of the mobile computing device 302, or may be a display of another computing device, a web site, or any other suitable display. The method 600 then proceeds to an end block and terminates.

Figure 7:
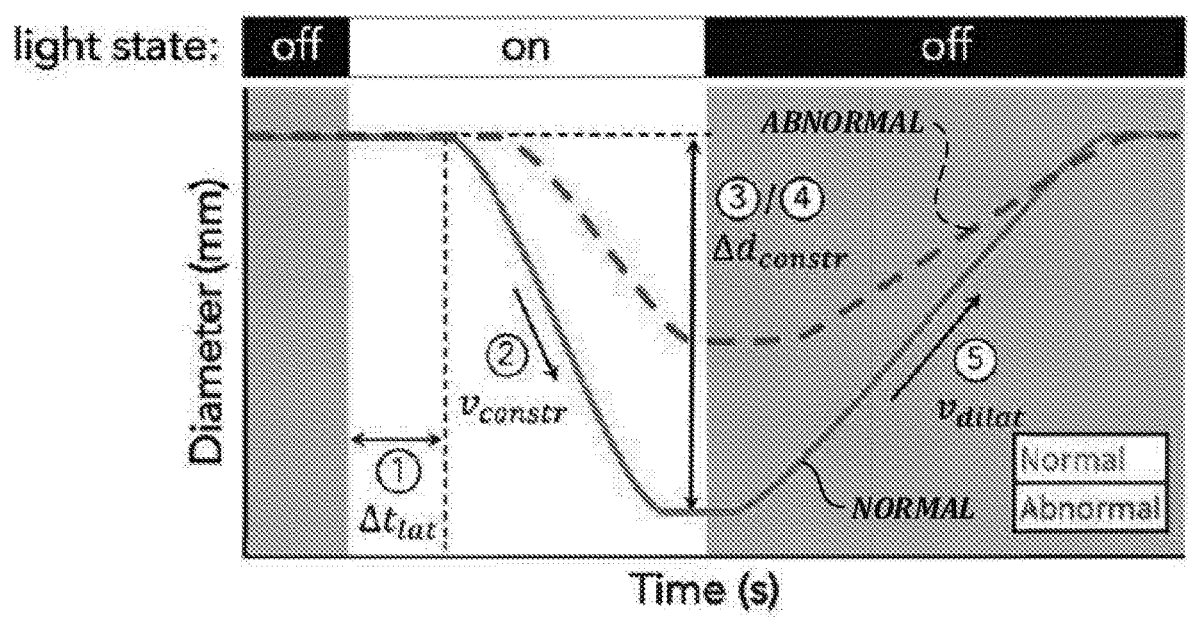
FIG. 7 illustrates an example embodiment of a presentation of a PLR curve based on the size of the at least one pupil over time generated by the pupil measurement engine according to various aspects of the present disclosure.

FIG. 7 illustrates an example embodiment of a presentation of a PLR curve based on the size of the at least one pupil over time generated by the pupil measurement engine 305 according to various aspects of the present disclosure. The PLR curve is annotated with the five common descriptive measures: (1) latency, (2) constriction velocity, (3) constriction amplitude, (4) constriction percentage, and (5) dilation velocity. An abnormal PLR curve with increased latency, slower velocities, and diminished amplitude is also included for comparison.

Figure 8:
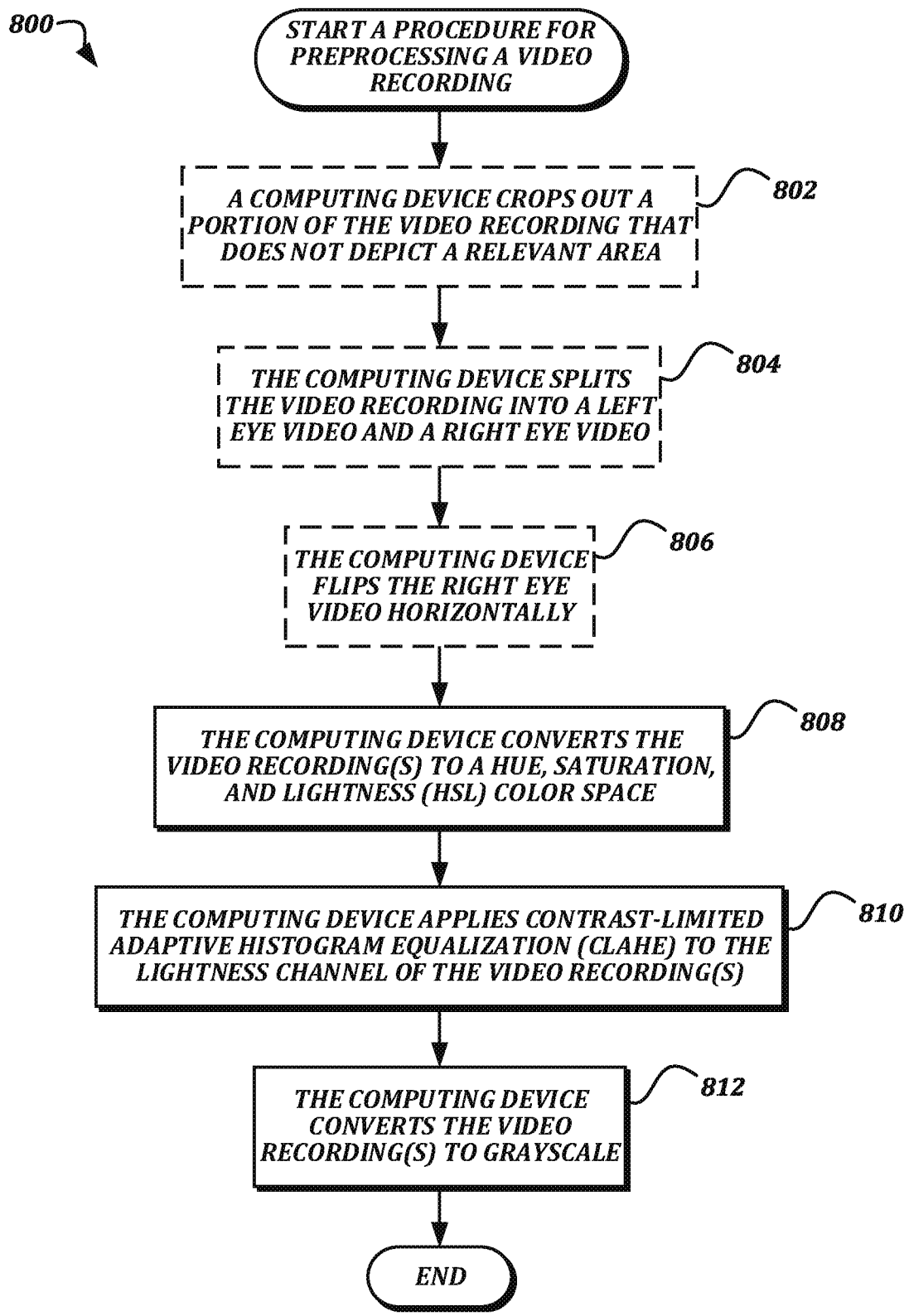
FIG. 8 is a flowchart that illustrates an example embodiment of a procedure for preprocessing a video recording according to various aspects of the present disclosure.

FIG. 8 is a flowchart that illustrates an example embodiment of a procedure for preprocessing a video recording according to various aspects of the present disclosure. The procedure 800 is an example of a procedure suitable for use at block 406 of FIG. 4 and block 604 of FIG. 6. The input to the procedure 800 is a video recording which may be generated as described above. The procedure 800 may be executed by any suitable computing device, and is typically executed by mobile computing device 302 or training computing device 304 as described above.

From a start block, the procedure 800 advances to optional block 802, where a computing device crops out a portion of the video recording that does not depict a relevant area. For example, if the video recording was generated using a box, it may be known that portions of the field of view of the camera 308 depict portions of the box. Accordingly, a portion of the video (such as the bottom third) may be cropped out. This is shown in the example image illustrated in FIG. 9. Optional block 802 is described as optional, because in some embodiments (particularly embodiments that do not use a box, or embodiments where the camera 308 is zoomed within the box to exclude the box from the field of view), a portion of the field of view may not consistently depict an irrelevant area.

Figure 9:
FIG. 9 illustrates an example of processing of an example video recording according to various aspects of the present disclosure.

Next, at optional block 804, the computing device splits the video recording into a left eye video and a right eye video. As shown in FIG. 9, the split may occur by splitting the video vertically down the middle. Optional block 804 is described as optional because in some embodiments, the video recording may depict only a single eye. At optional block 806, the computing device flips the right eye video horizontally. By flipping the right eye video horizontally as shown in FIG. 9, all of the videos will more closely match each other in shape and location, thereby improving the performance of the machine learning models. Optional block 806 is described as optional because the video recording may only depict a left eye, in which case the video recording does not have to be flipped. The above describes flipping the right eye video to match the left eye video. Of course, in some embodiments, the left eye video may be flipped to match the right eye video instead.

At block 808, the computing device converts the video recording(s) to a hue, saturation, and lightness (HSL) color space. The video may, for example, be captured and recorded in an sRGB or other color space. If the video recording is originally created in the HSL color space, the conversion of block 808 may not be necessary. At block 810, the computing device applies contrast-limited adaptive histogram equalization (CLAHE) to the lightness channel of the video recording(s). Using CLAHE avoids the pitfalls of global histogram equalization by dividing an image into small tiles (88 px in our case) and then equalizing only within those individual tiles.

At block 812, the computing device converts the video recording(s) to grayscale. The procedure 800 then advances to an end block and terminates, returning the preprocessed video recording(s) as a result of execution.

Pupil Screen does not include an explicit blinking detection step, so all frames are tested through the CNNs regardless of the whether the pupil is visible in them or not. That being said, the CNNs are only trained on images where the pupil is visible, so cases when the pupil is not visible lead to outlier results that are handled through the post-processing described above. We found that cases of blinking were not a significant source of error in PupilScreen's results, but a blink detector could be incorporated at the beginning of PupilScreen's pipeline or within the preprocessing procedure 800 so that irrelevant frames are accounted for sooner.

TESTING

We collected video recordings using the PupilScreen app and box to train its CNNs and evaluate its ability to track pupil diameter. Since our approach to segmenting pupils relies on CNNs, we require a large number of training examples from individuals with various pupil sizes and iris colors. This is difficult to attain through a patient population with TBI. Cases of TBI are limited, and the pupils of those with TBI usually stay a fixed size. Because of this, our networks are trained on data from healthy volunteers at the University of Washington and Harborview Medical Center.

TABLE 1

| Participant demographics (N = 42) | |
| --- | --- |
| SEX-N (%) | |
| Male 16 | (38.1%) |
| Female 26 | (61.9%) |
| IRIS COLOR-N (%) | |
| Blue 17 | (40.5%) |
| Brown 20 | (47.6%) |
| Mixed 5 | (11.9%) |

Our training dataset comes from 42 volunteers: 16 males and 26 females. Typical non-infrared computer vision-based systems are reliant on determining the border between the iris and the pupil, which is more obvious for those with light blue eyes than those with dark brown eyes. For this reason, it was important to recruit participants with various iris colors. Our study includes a balanced mix of iris colors: 17 blue, 20 brown, and 5 with a noticeable gradient between different colors. In most cases, the irises that were classified as mixed were light brown near the pupil but primarily blue.

Ideally, ethnicity should have no effect on PupilScreen's ability to measure the pupil diameter since the two are uncorrelated. Although we did not specifically ask participants for ethnicity information, we note that one-sixth of the participants had a darker skin complexion.

Figure 10:
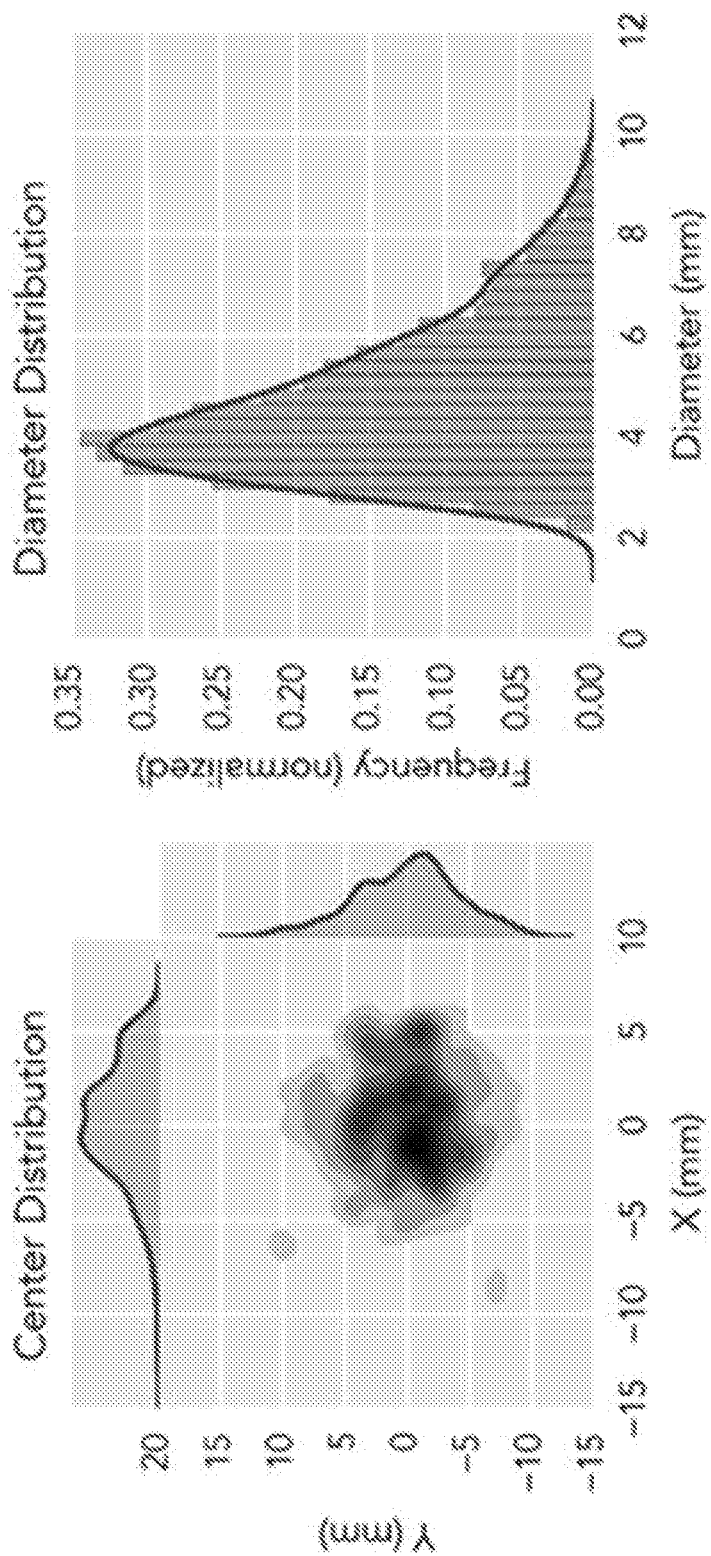
FIG. 10 illustrates distributions of test data used to verify performance of an embodiment of the present disclosure.

The left side of FIG. 10 shows the distribution of the pupil center location across all users after the video frames were cropped, flipped, and scaled to millimeters. The distribution is centered at the mean pupil center for reference. The distribution has a standard deviation of 3.22 mm in the x-direction. This spread can be attributed to variation in interpupillary distance and the fact that participants did not perfectly align their face within the PupilScreen box. The distribution has a standard deviation of 4.18 mm in the y-direction, which can also be attributed to different face shapes and the placement of the PupilScreen box relative to the participant's face.

Figure 11A:
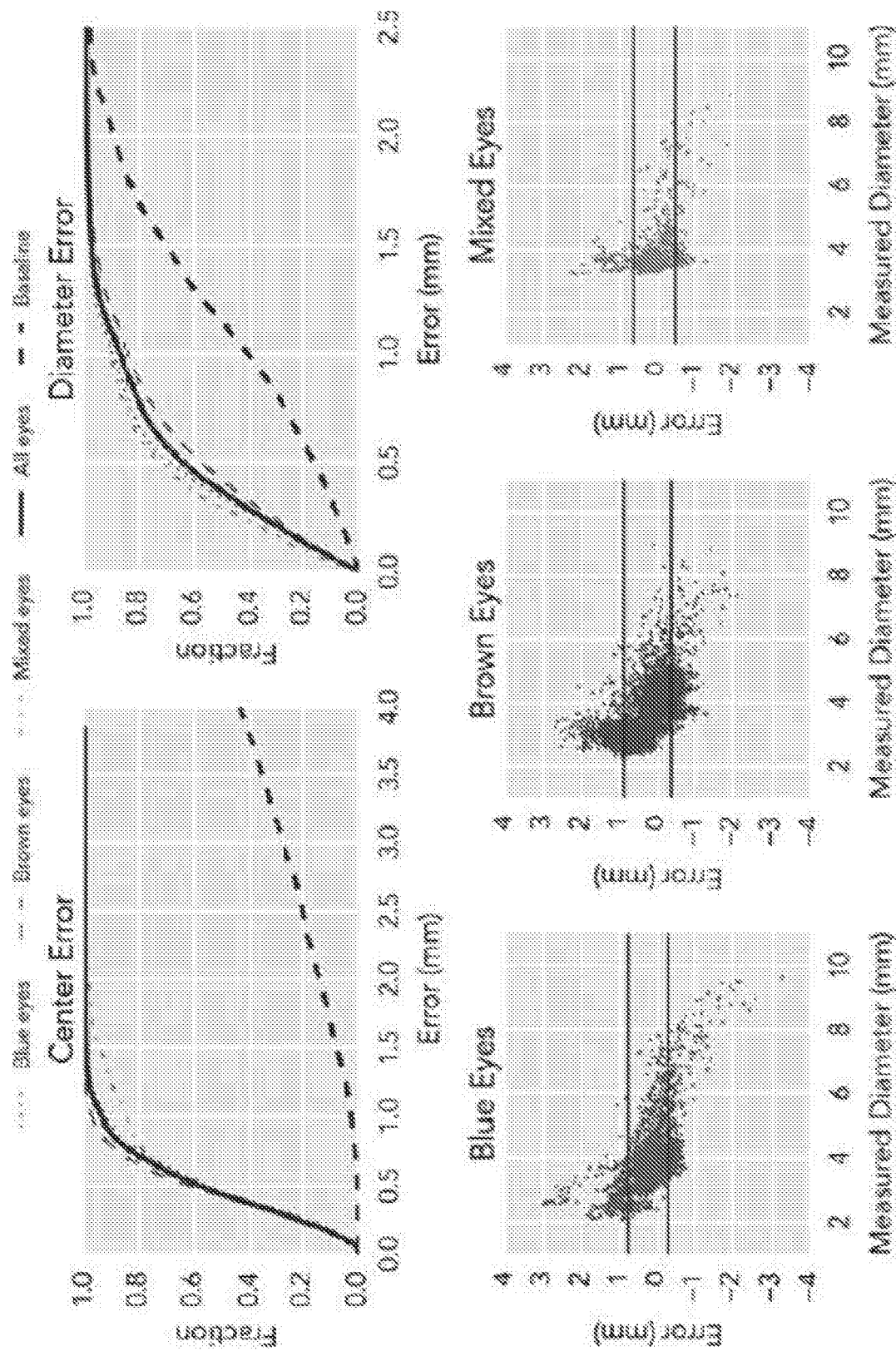
FIGS. 11A and 11B illustrate analysis of results gathered during testing of embodiments of the present disclosure.

The cumulative distribution functions (CDFs) at the top of FIG. 11A show the distribution of the absolute errors for the sequential network architecture. The thick dashed line in both plots compares the results to a baseline that assumes the mean predictions for all users; this is not meant to serve as a comparable algorithm, but rather ground the results relative to some other estimator. Improvement over the baseline demonstrates that the networks are learning more than just the mean value.

The top-left of FIG. 11A shows the CDF for the errors of the first network, which estimates the pupil center for a cropped input video frame. Across all users, the distribution of Euclidean errors has a median of 0.43 mm and a 90th percentile of 0.87 mm. The error distributions across the different iris colors are nearly identical. The magnitude of the error can partly be attributed to the pre-processing of the video frame. Input images are downsampled by a factor of 4, which reduces the resolution of the pupil center estimation to 0.31 mm. Despite the loss of resolution, the errors are well within the diameter of the iris (10-12 mm). In fact, most are within the smallest observed pupil diameters (~2 mm). Although it is ideal for the pupil to be centered in the image that is input to the second network, the most important result is that the eye always remains in the region of interest that is cropped around the center prediction. By jittering the training data, the second network is trained to handle shifted images.

The top-right of FIG. 11A shows a similar CDF plot for the errors of the second network, which estimates the pupil diameter given an image cropped using the pupil center output by the first network. Across all users, the distribution of absolute errors has a median of 0.36 mm and a 90th percentile of 1.09 mm. According to Meeker et al., the error of PupilScreen's diameter estimation is better than that of manual examination (0.5 mm), but worse than that of a clinical pupilometer (0.23 mm). To determine if the error of the first network leads to greater errors in the second network, we examined the accuracy of the second network given input images cropped around the ground truth pupil center. We found that there was little difference between using the predicted pupil centers and the ground truth pupil centers (50th:0.36 mm, 90th:1.19 mm vs. 50th:0.36 mm, 90th:1.15 mm). The fact that using the ground truth centers did not improve the accuracy of the pupil diameter estimation may be a byproduct of the fact that the training data was jittered, leading the network to be invariant to exact pupil location.

The Bland-Altmann plots in the bottom half of FIG. 11A show a different representation of the diameter prediction errors split across the different iris colors. In all cases, the sequential network architecture tends to overestimate the pupil diameter. If the CNN relies upon convolutional filters that look for edges, overestimation could be happening because those filters are more likely to respond to regions outside of the pupil's actual boundary. The mean pupil diameter errors are +0.24 mm, +0.27 mm, and +0.07 mm for blue, brown, and mixed eyes, respectively.

We find that the most extreme outliers belong to a small subset of participants who had particularly dark irises. We believe that this error can be reduced with more training data from participants with similarly dark irises.

Figure 11B:
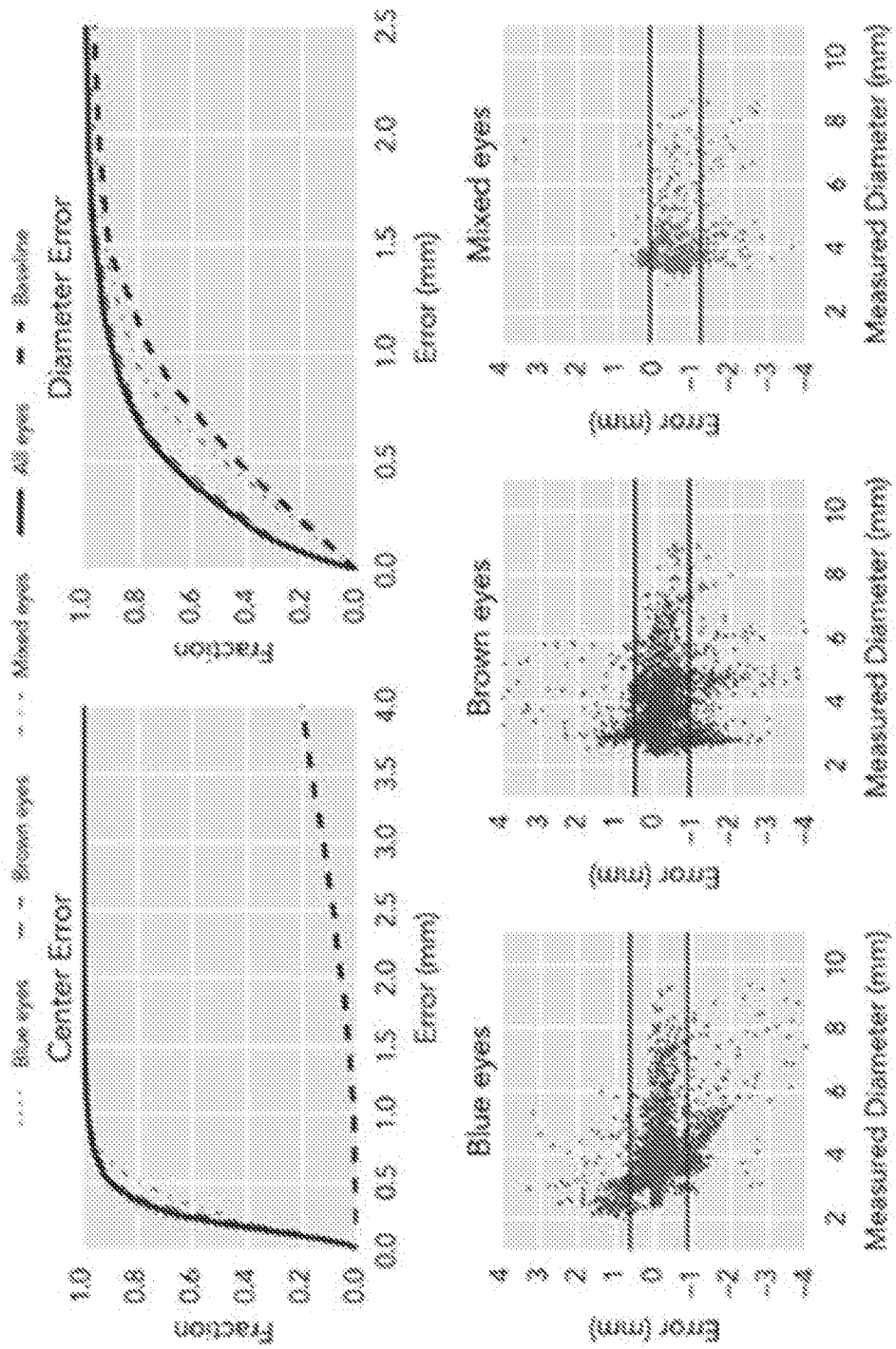

FIG. 11B shows the same performance measures for the fully convolutional architecture. The CDFs at the top of the figure show that the fully convolutional network was generally more accurate than using sequential networks. Across all users, the distribution of Euclidean errors for the pupil center has a median of 0.20 mm and a $90^{th}$ percentile of 0.50 mm. The distribution of absolute errors for the pupil diameter has a median of 0.30 mm, which is closer to the observed accuracy of a clinical pupilometer than the 0.36 mm median error of the sequential network architecture. Examining the Bland-Altmann plots in FIG. 11, we find that the fully convolutional architecture tends to underestimate the pupil diameter. The mean pupil diameter errors are −0.11 mm, −0.20 mm, and −0.55 mm for blue, brown, and mixed eyes, respectively. Beyond the inherent differences between the two architectures from a deep learning standpoint, one reason for the improved results could be the fact that explicit morphological operations could be performed on the pixel labels; rather than hoping that the network could learn some attribute in regards to smooth edges, it is easier exercise domain-knowledge and enforce such rules afterwards. The post-processing could also explain why this architecture underestimated diameters; although smoothing can remove protrusions from a jagged pupil boundary estimate, it can also shrink an otherwise correct, smooth pupil boundary estimate.

There is a noticeable difference between the results for different iris colors. For both architectures, images of brown eyes led to the worst results. The sequential network architecture had a median error of 0.41 mm and a 90th percentile error of 1.19 mm, and the fully convolutional architecture had a median error of 0.33 mm and a 90th percentile error of 1.14 mm. This may be because the boundary between the pupil and the iris is less noticeable for people with darker irises, so the convolutional filters in the networks are less likely to respond to the appropriate regions of the eye. We also hypothesize that this is the reason for why the measured diameter error for brown eyes does not correlate with the pupil size as it does with the lighter iris colors, a phenomenon noted by Meeker et al. when pupils were manually examined.

Figure 12:
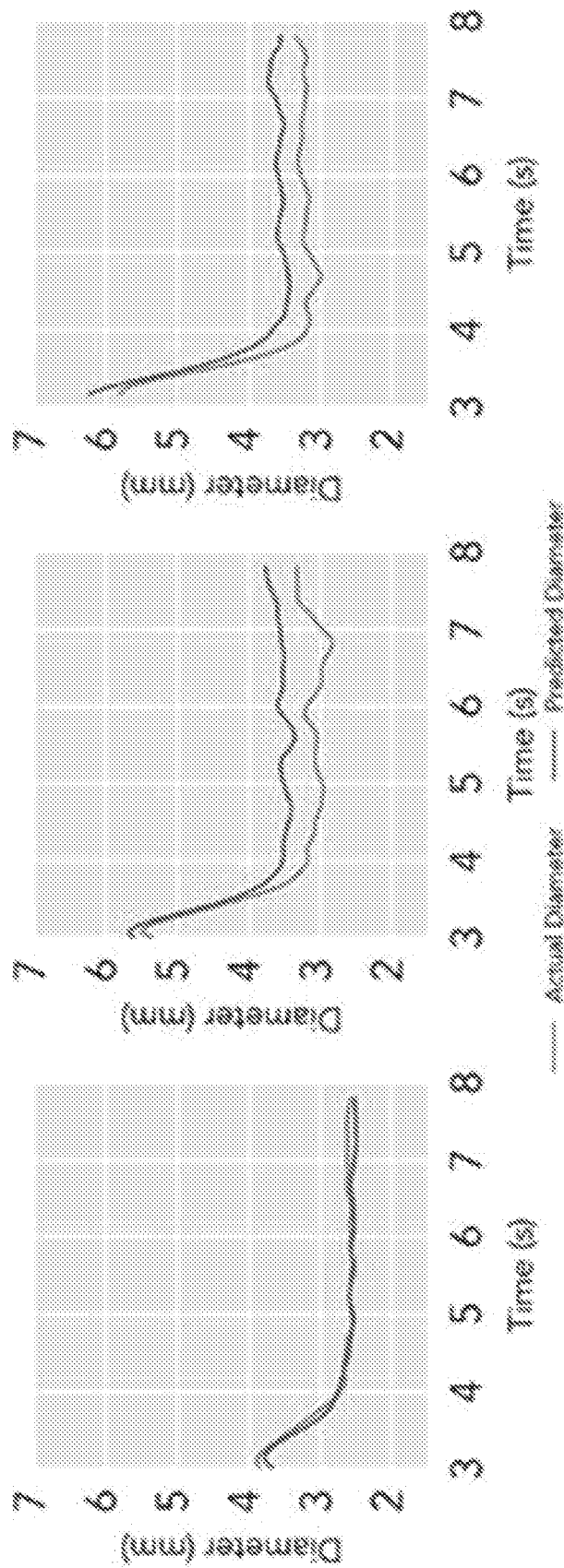
FIG. 12 compares several examples of PLR curves produced by an example embodiment of the present disclosure with ground truth PLR curves from manual annotations.

The outputs of PupilScreen's networks are useful once they are combined sequentially in PLR curves. For the sake of brevity, the results from here on out come from the fully convolutional architecture since it was slightly more accurate. To quantify how well the predicted PLR curves track the human-labeled PLR curves, their normalized cross-correlation was calculated. The average normalized cross-correlation across all videos is 0.91. FIG. 12 compares several examples of PLR curves produced by PupilScreen with ground truth PLR curves from manual annotations. The left chart is an example where PupilScreen accurately estimates all PLR metrics. The center chart is an example where PupilScreen accurately estimates the maximum constriction velocity, but underestimates the constriction amplitude and percentage. The right chart is an example where PupilScreen accurately estimates the constriction amplitude and maximum constriction velocity, but underestimates the constriction percentage.

Table 2 describes how well PupilScreen is able to predict PLR metrics relative to those measured from the manually labeled dataset. Table 2 also shows the range of those metrics across all participants as a point of comparison for the error magnitude. PupilScreen can track constriction amplitude with a mean error of 0.62 mm, constriction percentage within a mean error of 6.43%, and max constriction velocity with a mean error of 1.78 mm/s. As a point of comparison from the literature, an evaluation of PupilWare by Rafiqi et al. demonstrated that their system tracked constriction and dilation percentages with an accuracy such that 90% of their predictions fell within 10% of the ground truth. However, there are many differences between PupilWare and PupilScreen that make these results difficult to compare. PupilScreen was evaluated on many more participants than PupilWare (42 vs. 9), but the evaluation of PupilWare aggregated a time series of percent change values rather than the single summary statistic like Pupil Screen. The two systems are also intended for different applications. PupilWare is designed to track changes in pupil size attributed to varying cognitive load, which tend to be smaller in amplitude than the changes induced in PupilScreen.

TABLE 2

PLR metric evaluation

| CONSTRICTION AMPLITUDE-mm | |
|---|---|
| Ground truth range | 0.32-6.02 |
| Mean absolute error | 0.62 |
| Standard deviation of absolute error | 0.72 |
| CONSTRICTION PERCENTAGE-% | |
| Ground truth range | 6.21-62.00 |
| Mean absolute error | 6.43 |
| Standard deviation of absolute error | 6.74 |
| MAX CONSTRICTION VELOCITY-mm/s | |
| Ground truth range | 1.37-8.99 |
| Mean absolute error | 1.78 |
| Standard deviation of absolute error | 0.67 |

Examining the predicted PLR curves further provides insight into the nature of these errors. The center and right plots in FIG. 12 show cases where a repeated error across frames led to the inaccurate estimation of some PLR metrics, but not others. In the center, PupilScreen correctly tracks the pupil diameter during constriction, but then overestimates the final diameter of the pupil after constriction. The max constriction velocity is correctly estimated in these situations, but the constriction amplitude and percentage are not. On the right, PupilScreen follows the ground truth PLR curve with a roughly constant offset. This means that although the absolute estimate of the pupil diameter may be off, the change between the minimum and maximum pupil remains unchanged. This behavior only affects the constriction percentage since it relies on an absolute baseline; the constriction velocity and amplitude remain unaffected. Although not shown in FIG. 12, errors in all three metrics can also be attributed to pupil diameter predictions that deviated from nearby frames in a manner that failed PupilScreen's outlier criteria but were significant enough to create a deflection in the filtered PLR curve.

To gauge PupilScreen's diagnostic efficacy, we supplemented our dataset with videos from six patients at Harborview Medical Center's trauma ward and neuro-intensive care unit (neuro-ICU). These individuals had sustained significant head trauma, but were stable enough at the time to be recruited for the study. Their doctors and nurses knew beforehand that they had non-reactive pupils. Non-reactive pupils are frequently observed in patients whose condition is unstable, making it difficult to use our research prototype without interfering with the clinician's workflow. As before, three videos were recorded for each patient; however, there were complications in collecting these videos, including the inability of the patients to keep their eyes open and the inability of the clinician to maintain the position of the box while recording the videos. Because of these issues, only 24 of the 36 possible PLR curves (3 videos per patient×2 eyes per patient×6 patients) were suitable for analysis.

Figure 13:
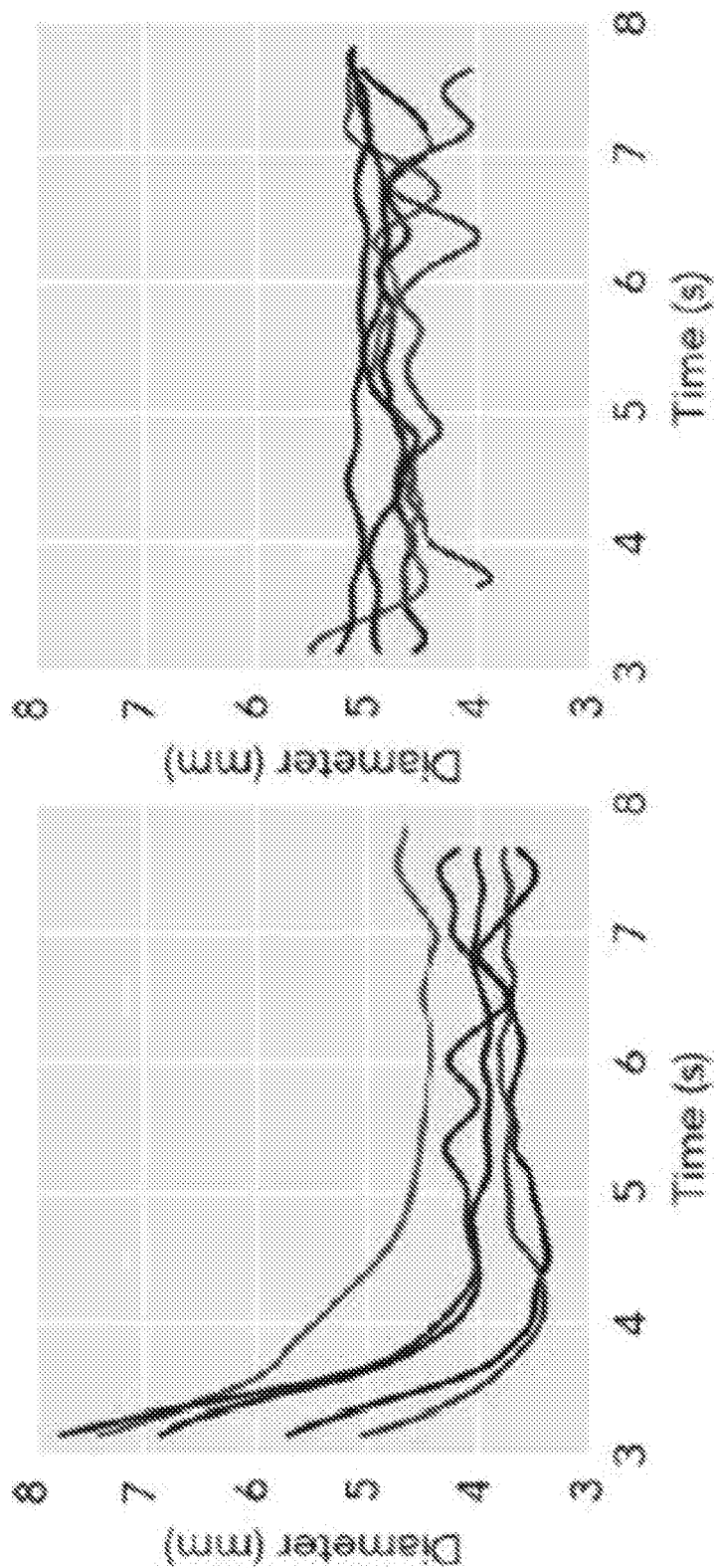
FIG. 13 shows examples of both responsive and non-responsive pupils that were collected with an embodiment of the present disclosure.

To evaluate PupilScreen's accuracy on non-reactive pupils, we randomly selected one of the folds created during our initial training and analysis. The patient videos were processed using the CNNs that were trained on that fold's training data to produce pathologic PLR curves. An equal number of healthy PLR curves were generated using randomly selected videos from that fold's test set. Using the same network for both sets of videos guaranteed that the PLR curves were generated from networks that were trained on the same data. FIG. 13 shows examples of both responsive and non-responsive pupils that were collected with PupilScreen. The PLR curves from healthy individuals have a noticeable exponential decay, whereas the PLR curves from the patients do not.

The PLR curves were anonymized, shuffled, and then sent to two clinicians familiar with pupilometry. The clinicians were asked to classify the PLRs as either "responsive" or "non-responsive". They were not told how many curves would be in each category, nor were they shown the video recordings themselves. The first clinician was able to correctly classify every curve in our dataset. The second clinician misclassified one non-responsive PLR curve as responsive. In that particular case, PupilScreen estimated that the person's pupil constricted in a slow and almost linear manner, but by a significant amplitude. The second clinician also misclassified one responsive PLR curve as non-responsive, again, due to the borderline pupil constriction amplitude.

Throughout our design process, we asked clinicians about their personal experiences with pupilometry and for feedback on PupilScreen's design. These clinicians included surgeons, nurses, and other personnel at the Harborview Medical Center's neuro-ICU. Although PupilScreen is proposed as a tool to be used by team doctors and parents, clinicians who work with TBI are far more familiar with existing pupilometry methods and their tradeoffs and could provide far more insight beyond novelty.

One of the surprising findings early on was that although the clinicians were familiar with the purpose of a pupilometer and its advantages over a penlight test, the pupilometer was hardly used in the clinical setting. The pupilometer was mainly used to track changes in PLR over a long period of time to identify worsening injuries as quickly as possible in otherwise unresponsive patients. For diagnosis or triage, penlights are strongly preferred for their simplicity and ease of access, despite the limited precision and lack of consistency they afford. As one clinician stated, "If whatever you ask an EMT to do adds twenty seconds or so, it's not worth it". In fact, we found that some clinicians use their smartphone's flash instead of a penlight, validating aspects of our idea. When we asked the clinicians about the prospect of PupilScreen's convenience, they were excited by the idea of a smartphone app that would be in their pockets at all times.

While illustrative embodiments have been illustrated and described, it will be appreciated that various changes can be made therein without departing from the spirit and scope of the invention.

The invention claimed is:

1. A system, comprising:
   a mobile computing device comprising a camera, a display, and a non-transitory computer-readable medium, wherein the computer-readable medium has computer-executable instructions stored thereon which, in response to execution by at least one processor of the mobile computing device, cause the mobile computing device to perform actions comprising:
   obtaining a video recording of a left eye of a subject and a right eye of the subject using the camera;
   preprocessing the video recording by splitting the video recording horizontally into a left eye video recording and a right eye video recording and horizontally flipping the left eye video recording or the right eye video recording;
   using a machine learning model to detect changes in at least one of a size of a pupil of the left eye and a size of a pupil of the right eye during the video recording; and
   presenting the detected changes in at least one of the size of the pupil of the left eye and the size of the pupil of the right eye on the display.

2. The system of claim 1, wherein the machine learning model includes at least a first convolutional neural network (CNN) configured to output an X coordinate of a pupil center and a Y coordinate of a pupil center and a second CNN configured to output a pupil diameter.

3. The system of claim 2, wherein using the machine learning model to detect changes in at least one of the size of the pupil of the left eye and the size of the pupil of the right eye during the video recording includes, for at least one of the left eye video recording and the right eye video recording:
   providing a down-sampled version of the eye video recording to the first CNN;
   cropping the eye video recording based on the X coordinate and the Y coordinate output by the first CNN; and
   providing the cropped eye video recording to the second CNN.

4. The system of claim 2, wherein at least one of the first CNN and the second CNN includes five convolutional layers and three fully connected layers.

5. The system of claim 4, wherein each convolutional layer includes a rectified linear (ReLU) activation function followed by 2×2 mean-pooling layers.

6. The system of claim 1, wherein preprocessing the video recording further includes
   cropping out a bottom third of the video recording.

7. The system of claim 1, wherein preprocessing the video recording further includes:
   converting the video recording to a hue, saturation, and lightness (HSL) color space if the video recording is not already in the HSL color space;
   applying contrast-limited adaptive histogram equalization (CLAHE) to the lightness channel of the video recording; and
   converting the video recording to grayscale.

8. The system of claim 1, further comprising a box configured to hold the mobile computing device in a fixed relationship to the left eye of the subject and the right eye of the subject, to screen out ambient light from the video recording, and to hold a filter over the light source of the mobile computing device.

9. The system of claim 1, wherein presenting the detected changes in at least one of the size of the pupil of the left eye and the size of the pupil of the right eye on the display includes presenting at least one dilation curve, and wherein presenting the at least one dilation curve includes presenting the at least one dilation curve along with a baseline dilation curve to assist a diagnosis of a brain injury based on differences between the at least one dilation curve and the baseline.

10. The system of claim 1, wherein presenting the detected changes in at least one of the size of the pupil of the left eye and the size of the pupil of the right eye on the display includes presenting a first dilation curve for the left eye along with a second dilation curve for the right eye to assist a diagnosis of a brain injury based on differences between the first dilation curve and the second dilation curve.

11. A non-transitory computer-readable medium having computer-executable instructions stored thereon that, in response to execution by one or more processors of a computing device, cause the computing device to perform actions for measuring changes in a size of a pupil over time in response to a light stimulus, the actions comprising:
   receiving, by the computing device, a video recording of a left eye and a right eye of a subject, wherein the video recording was recorded by a visible light camera;
   preprocessing the video recording by splitting the video recording horizontally into a left eye video recording and a right eye video recording and horizontally flipping the left eye video recording or the right eye video recording;
   using, by the computing device, a machine learning model to detect changes in at least one of a size of a pupil of the left eye and a size of a pupil of the right eye during the video recording; and
   providing, by the computing device, the detected changes in at least one of the size of the pupil of the left eye and the size of the pupil of the right eye for presentation on a display.

12. The computer-readable medium of claim 11, wherein using the machine learning model to detect changes in at least one of the size of the pupil of the left eye and the size of the pupil of the right eye during the video recording includes, for at least one eye video recording:
   providing a down-sampled version of the eye video recording to a first convolutional neural network (CNN) configured to output an X coordinate of a pupil center and a Y coordinate of a pupil center;
   cropping the eye video recording based on the X coordinate and the Y coordinate output by the first CNN; and
   providing the cropped eye video recording to a second CNN configured to output a pupil diameter.

13. The computer-readable medium of claim 11, wherein preprocessing the video recording further includes
cropping out a bottom third of the video recording.

14. The computer-readable medium of claim 11, wherein preprocessing the video recording further includes:
converting the video recording to a hue, saturation, and lightness (HSL) color space if the video recording is not already in the HSL color space;
applying contrast-limited adaptive histogram equalization (CLAHE) to the lightness channel of the video recording; and
converting the video recording to grayscale.

* * * * *